(12) United States Patent
Tsubaki et al.

(10) Patent No.: US 7,567,648 B2
(45) Date of Patent: Jul. 28, 2009

(54) SYSTEM OF GENERATING STEREOSCOPIC IMAGE AND CONTROL METHOD THEREOF

(75) Inventors: Hidetoshi Tsubaki, Utsunomiya (JP); Toshiyuki Sudo, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 240 days.

(21) Appl. No.: 11/147,080

(22) Filed: Jun. 7, 2005

(65) Prior Publication Data

US 2006/0039529 A1 Feb. 23, 2006

(30) Foreign Application Priority Data

Jun. 14, 2004 (JP) ............................. 2004-176153

(51) Int. Cl.
*A61B 6/02* (2006.01)
(52) U.S. Cl. ....................................... 378/41
(58) Field of Classification Search .................... 378/41
See application file for complete search history.

(56) References Cited

U.S. PATENT DOCUMENTS

| 4,987,487 | A | 1/1991 | Ichinose |
| 6,023,277 | A | 2/2000 | Osaka |
| 6,256,372 | B1 | 7/2001 | Aufrichtig |
| 6,268,862 | B1 | 7/2001 | Uchiyama |
| 6,359,961 | B1 | 3/2002 | Aufrichtig |
| 7,369,641 | B2 * | 5/2008 | Tsubaki et al. ............. 378/41 |
| 2002/0067356 | A1 | 6/2002 | Sudo |
| 2005/0053192 | A1 * | 3/2005 | Sukovic et al. ............. 378/41 |

FOREIGN PATENT DOCUMENTS

| JP | 2-50145 A | 2/1990 |
| JP | 9-245192 A | 9/1997 |
| JP | 10-232665 | 9/1998 |
| JP | 2000-287958 A | 10/2000 |
| JP | 2002-171536 A | 6/2002 |
| JP | 2003-209858 A | 7/2003 |

OTHER PUBLICATIONS

Natsuko Bandai, "New Technology for Chest Radiography by Use of Three Dimensional", Journal of Chubu division of Japanese Society of Radiological Technology vol. 3 No. 1, 2001.
Marc Levory, et al., "Light Field Rendering", Proceedings of Special Interest Group for Computer Graphics (SIGGRAPH), pp. 31-42, 1996.

* cited by examiner

*Primary Examiner*—Chih-Cheng G Kao
(74) *Attorney, Agent, or Firm*—Canon U.S.A., Inc. I.P. Division

(57) ABSTRACT

A stereoscopic-image generating system includes a radiation source, an image pickup device adapted to acquire information on a transmissive radiation ray transmitted through an object, the transmissive radiation ray being emitted from the radiation source, and a control device adapted to acquire presentation parameters of a presentation device which present a stereoscopic image based on the information on the transmissive radiation ray and to control a relative position of the radiation source with respect to the image pickup device in the acquisition of the information on the transmissive radiation ray based on the presentation parameters.

7 Claims, 12 Drawing Sheets

FIG. 1A
FIG. 1B
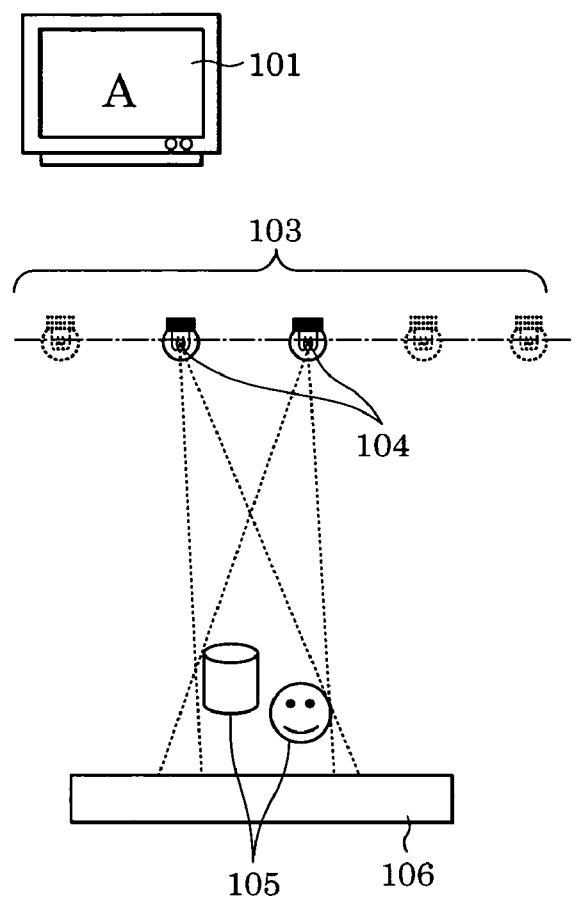
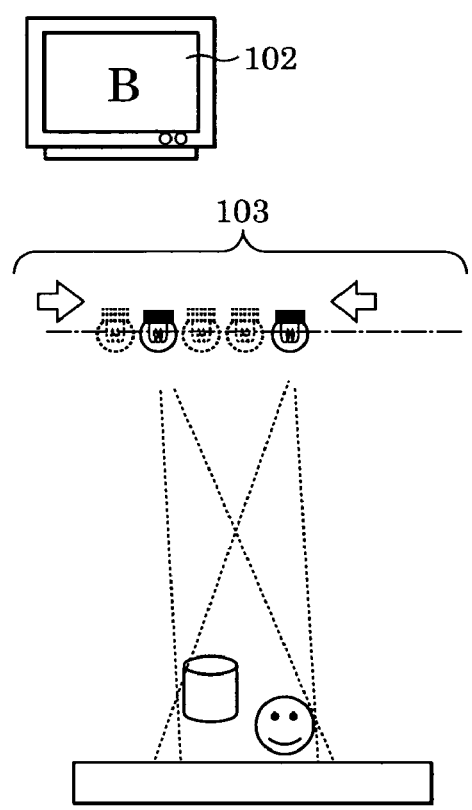

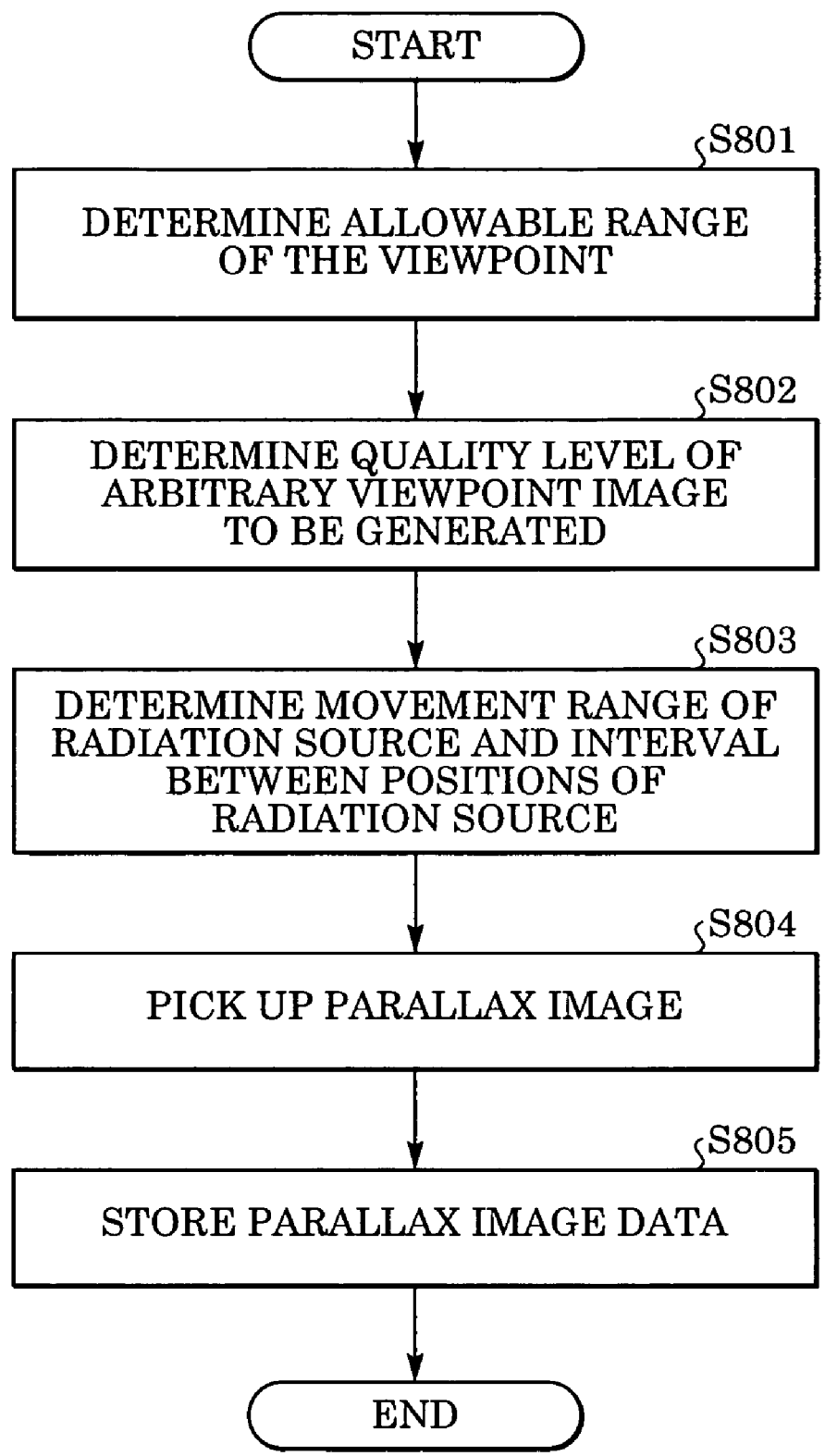

FIG. 10A
FIG. 10B
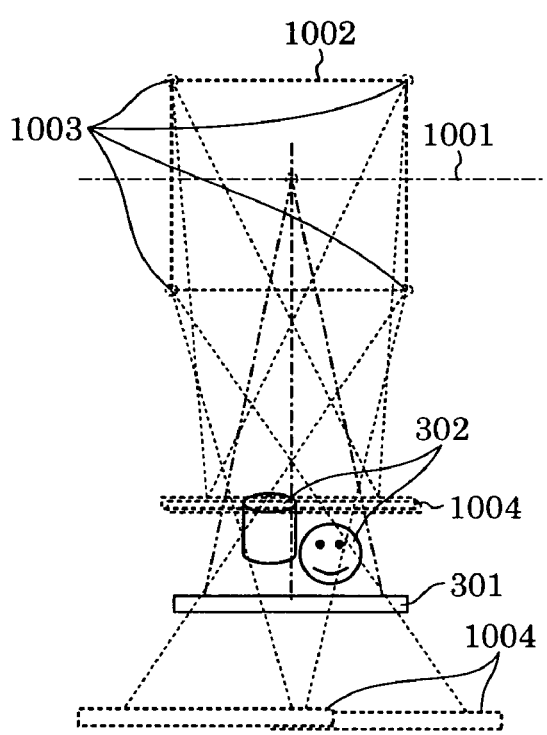
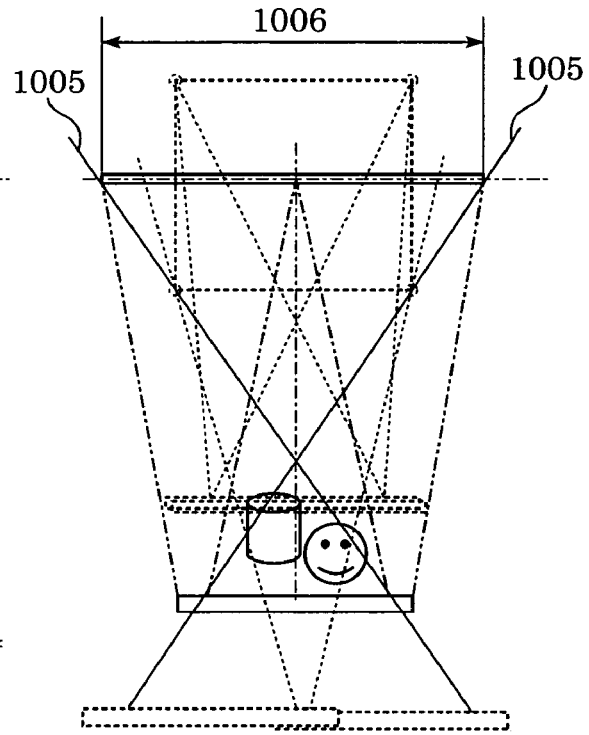

SYSTEM OF GENERATING STEREOSCOPIC IMAGE AND CONTROL METHOD THEREOF

BACKGROUND OF THE INVENTION

1. Field of the Invention

The present invention relates to a system of irradiating an object with a radiation ray to pick up a rear-projected image and of three-dimensionally presenting the picked-up image.

2. Description of the Related Art

Irradiating an object with X-rays to pick up rear-projected images is common in, for example, medical diagnosis. However, since the projected images are picked up, the information concerning all the regions which the radiation rays pass through is superimposed and, therefore, it is difficult to determine the distribution of diseased parts on a three-dimensional space.

Technologies in which an object is irradiated with X-rays in all directions to pick up rear-projected images, the data is reconstructed to acquire voxel data, and tomographic images on an arbitrary slice plane are displayed by rendering have also been developed. With such technologies, it is possible to easily determine three-dimensional positions of diseased parts. However, there are problems in that artifact contamination is caused in the reconstruction of the data and that the resolution of the reconstructed images becomes lower than that of the picked-up images.

One technique for resolving such problems is so-called "stereoscopic observation". The stereoscopic observation, in which rear-projected images are directly observed, has the advantages of observing high-resolution images and of easily determining the stereoscopic depth of diseased parts by stereoscopic vision using parallax.

A system of presenting stereoscopic images, applicable to the presentation of images in the stereoscopic observation, is disclosed in, for example, U.S. Pat. No. 6,256,372 (Aufrichtig, et al.) and U.S. Pat. No. 6,359,961 (Aufrichtig, et al.). In such a system of presenting stereoscopic images, a radiation source is moved on a surface having an arbitrary shape to pick up images (parallax images) from multiple viewpoints in time division multiplexing. Observing two arbitrary parallax images from the corresponding two viewpoints achieves observation of a stereoscopic image.

However, the difficulty in directly performing the stereoscopic observation of the images varies among individuals. Accordingly, it is preferable to use three-dimensional display devices that allow anyone to easily perform the stereoscopic observation. Medical diagnosis by the stereoscopic observation using such three-dimensional display devices is proposed in academic societies (refer to Natsuko Bandai, 2001, "Sanjigen-display wo mochiita atarashii kyoubu X-sen satsuei-ho", Journal of Chubu division of Japanese Society of Radiological Technology Vol. 3 No. 1).

In a general digital photography field, technologies of generating arbitrary viewpoint images based on image-based rendering, such as ray interpolation, which technologies are capable of generating images of viewpoints arbitrarily selected, are known (U.S. Pat. No. 6,268,862 (Uchiyama, et al.) and Marc Levoy et al., 1996, "Light Field Rendering" Proceedings of Special Interest Group for Computer Graphics (SIGGRAPH)).

There are various presentation devices, such as three-dimensional displays and three-dimensional printers, which output stereoscopic images. In order to achieve a similar stereoscopic view in the various presentation devices, it is necessary to pick up rear-projected images by a trial-and-error method in consideration of the characteristics of the individual presentation devices.

For example, it is necessary to pick up rear-projected images in consideration of technical matters, including the difference in the number of viewpoints among three-dimensional displays, a variation in the ratio of the angle of view at the time of input to the angle of view at the time of output, the parallax limit within which the images can be presented, and the difference in the method of emitting light rays. Accordingly, when persons who have no technical knowledge about the three-dimensional displays take the images, the stereoscopic view of the stereoscopic images is varied, thus giving different impressions to an observer. In other words, in order to present natural stereoscopic views, it is necessary to pick up images of an object in consideration of the parameters of the three-dimensional displays and, also, of the parameters of the image pickup device.

Also in the application of the technologies of generating arbitrary viewpoint images to the three-dimensional display of rear-projected images, it is necessary to calculate multiple virtual radiation source positions in consideration of the display parameters of the three-dimensional display devices, a virtual viewpoint position, which is a candidate for the observation viewpoint, and the image pickup parameters of the image pickup device and to generate the rear-projected images corresponding to the virtual radiation source positions, as in the normal display of stereoscopic images. Hence, it is difficult to provide the stereoscopic images having expected stereoscopic views only by simply applying the above technologies.

In order to realize the generation of arbitrary viewpoint images, in which the virtual viewpoint positions can be freely varied within a predetermined range, storage of a group of original images, picked up while the radiation source is moved to multiple positions, is required as a preparatory work. However, since there is no guideline on how to select the positions of the radiation source, an excessive number of original images can be picked up. The pickup of the excessive number of original images causes problems in that the radiation dosage to the object is increased, it takes excessive time to pick up the images, and an excessive amount of storage or photographic material is consumed. In contrast, the number of the original images that is too small can cause a reduction in the quality of the stereoscopic images.

SUMMARY OF THE INVENTION

According to a first aspect, the present invention provides a stereoscopic-image generating system including a radiation source, an image pickup device adapted to acquire information on a transmissive radiation ray transmitted through an object, the transmissive radiation ray being emitted from the radiation source, and a control device adapted to acquire presentation parameters of a presentation device which present a stereoscopic image based on the information on the transmissive radiation ray and to control a relative position of the radiation source with respect to the image pickup device in the acquisition of the information on the transmissive radiation ray based on the presentation parameters.

According to a second aspect, the present invention provides a stereoscopic-image generating system including a radiation source, an image pickup device adapted to acquire information on a transmissive radiation ray transmitted through an object, the transmissive radiation ray being emitted from the radiation source, a control device adapted to vary a relative position of the radiation source with respect to the image pickup device to cause the image pickup device to acquire the information on the transmissive radiation ray, a storage device adapted to store the information on the transmissive radiation ray, a virtual radiation-source-position determining device adapted to acquire presentation parameters of a presentation device, the presentation device presenting a stereoscopic image, to determine a plurality of virtual radiation source positions in accordance with the presentation parameters, and a processing device adapted to select or generate rear-projected images corresponding to the virtual radiation source positions from the information on the transmissive radiation ray stored in the storage device to cause the presentation device to present the stereoscopic image based on the selected or generated rear-projected images.

According to a third aspect, the present invention provides a control method of a stereoscopic-image generating system including an image pickup device that acquires information on a transmissive radiation ray transmitted through an object, the transmissive radiation ray being emitted from a radiation source. The control method includes acquiring presentation parameters of a presentation device that presents a stereoscopic image based on the information on the transmissive radiation ray and controlling a relative position of the radiation source with respect to the image pickup device in the acquisition of the information on the transmissive radiation ray based on the presentation parameters.

According to a fourth aspect, the present invention provides a control method of a stereoscopic-image generating system including an image pickup device that acquires information on a transmissive radiation ray transmitted through an object, the transmissive radiation ray being emitted from a radiation source. The control method includes varying a relative position of the radiation source with respect to the image pickup device to cause the image pickup device to acquire the information on the transmissive radiation ray, storing the information on the transmissive radiation ray, acquiring presentation parameters of a presentation device presenting a stereoscopic image, determining a plurality of virtual radiation source positions in accordance with the presentation parameters, selecting the information on the transmissive radiation ray corresponding to the virtual radiation source positions from among the stored information, and causing the presentation device to present the stereoscopic image based on the selected information.

Further features and advantages of the present invention will become apparent from the following description of exemplary embodiments with reference to the attached drawings.

BRIEF DESCRIPTION OF THE DRAWINGS

FIGS. 1A and 1B are schematic diagrams showing the operation of a stereoscopic-image generating system according to a first embodiment of the present invention.

FIGS. 8A and 8B are flowcharts showing the operation of a stereoscopic-image generating system according to a second embodiment of the present invention.

FIGS. 10A and 10B illustrates the relationship between the allowable movement range of a viewpoint and the movement range of a radiation source in the generation of an arbitrary viewpoint image, according to the second embodiment of the present invention.

DESCRIPTION OF THE EMBODIMENTS

The present invention provides a system of generating stereoscopic images and a control method of the system, where the system is capable of easily presenting the stereoscopic images having natural stereoscopic views in various presentation devices and is capable of efficiently generating arbitrary viewpoint images with high quality. Embodiments of the present invention are described below with reference to the attached drawings.

First Embodiment

Figure 2:
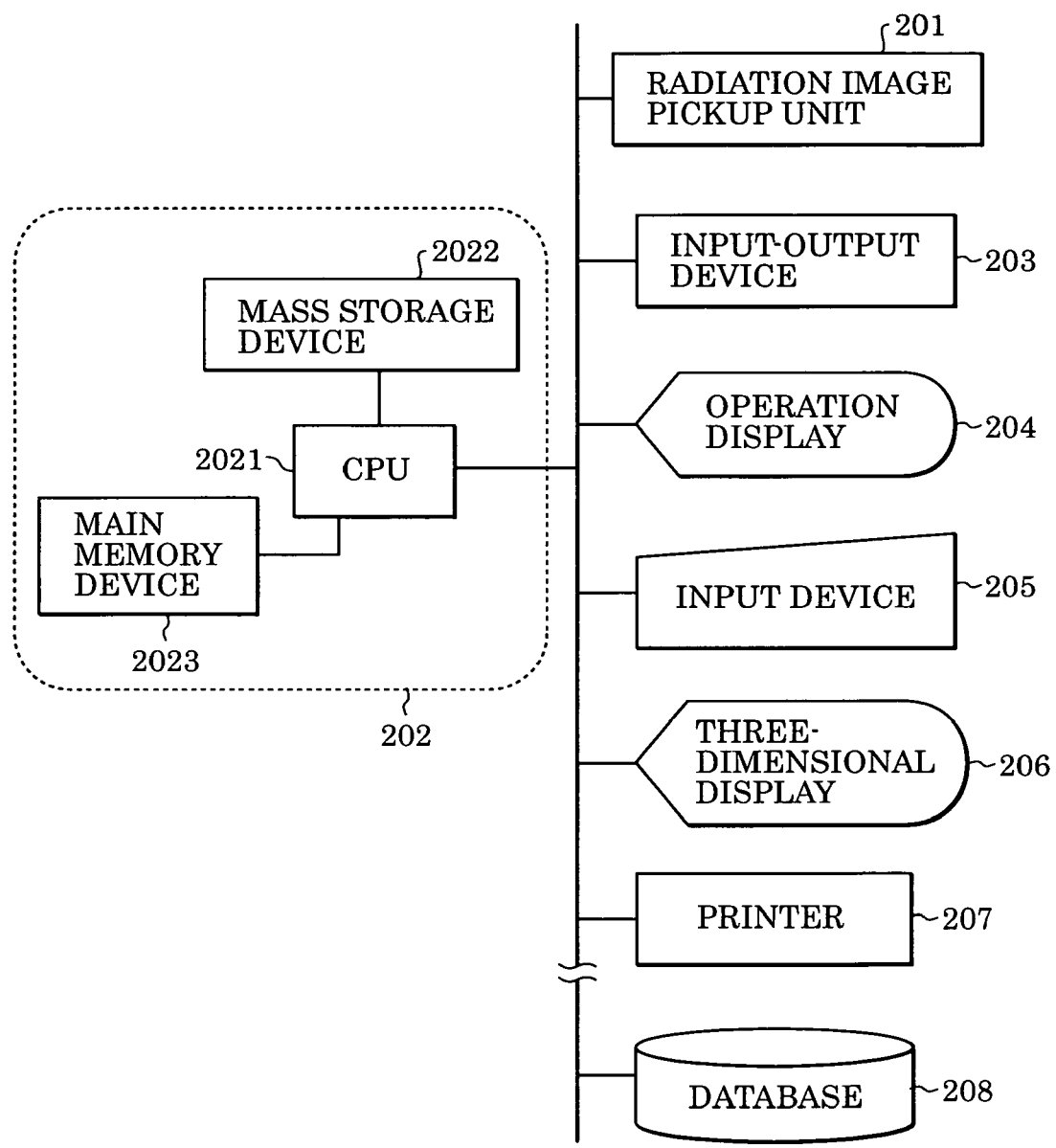
FIG. 2 is a block diagram showing the structure of the stereoscopic-image generating system according to the first embodiment of the present invention.
Figure 3:
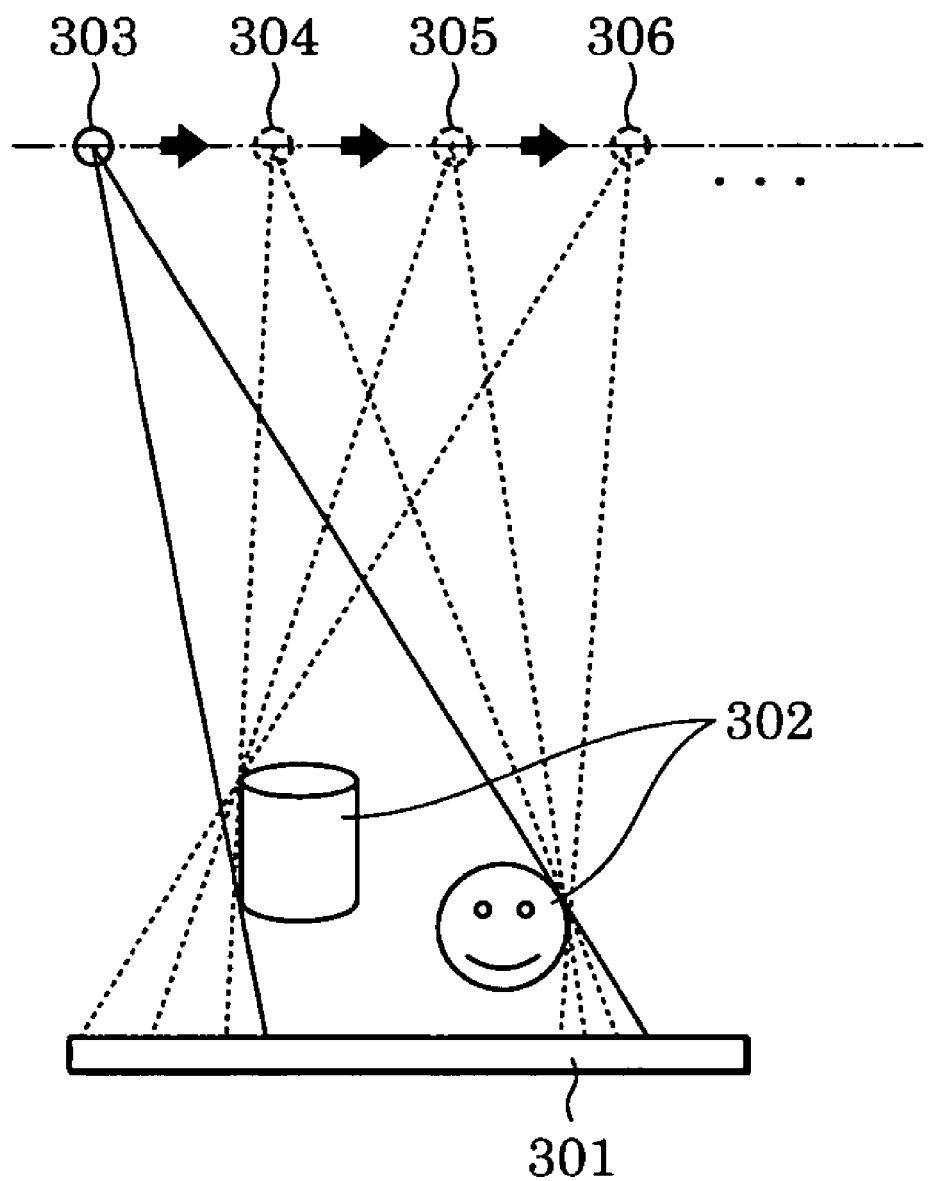
FIG. 3 is a schematic diagram showing the structure of a radiation image pickup unit according to the first embodiment of the present invention.

FIG. 2 is a block diagram showing the structure of a system of generating a stereoscopic image (hereinafter referred to as a stereoscopic-image generating system), according to a first embodiment of the present invention. Referring to FIG. 2, the stereoscopic-image generating system includes a radiation image pickup unit 201 converting a rear-projected image picked up by irradiation with radioactive rays (for example, X-rays) into an electrical signal. As shown in FIG. 3, the radiation image pickup unit 201 includes an image pickup device 301 having a radiation receiving element (e.g., a photoelectric transducer which converts the radioactive rays into a electrical signal) and a radiation source 303 capable of moving with respect to the image pickup device 301. The radiation source 303 moves toward positions 304, 305, 306, .... Here, neither the radiation image pickup unit 201 nor the image pickup device 301 need to pick-up an object image. That is, there is no need for the object and the radiation receiving element to have an optically conjugate spatial relationship. The radiation image pickup unit 201 and the image pickup device 301 need only have a receiving unit which receives the radioactive rays transmitted through the object, the radioactive rays being emitted from the radiation source 303, by the radiation receiving element and a storing unit which stores information on the received light quantity (e.g., a converting unit for converting the radioactive rays into an electrical signal and storing the electrical signal). In that case, the information on a distribution of the radioactive rays (a light quantity distribution) received by the radiation receiving element is called images. That is, the radiation image pickup unit 201 and the image pickup device 301 do not picking up an object image by the radiation receiving element arranged in the conjugate position for the object. The radiation image pickup unit 201 and the image pickup device 301 need only contain a unit (radiation receiving element) which can receive the radiation ray (transmissive radioactive rays) transmitted through the object, the radioactive rays being emitted from the radiation source, and can measure the light quantity of the transmissive radioactive rays or information on two-dimensional distribution of the light quantity (in this embodiment, the information is called images).

Although the radiation source 303 is moved on a flat surface in the first embodiment, the radiation source 303 may be moved on a quadric surface. Although one radiation source 303 is moved to vary the relative positional relationship between the radiation source 303 and the image pickup device 301 according to the first embodiment, switching between multiple radiation sources arranged on a flat surface or a quadric surface may vary the relative positional relationship between the radiation source and the image pickup device 301. Furthermore, radiation source 303 may be vertically moved with respect to the radiation receiving surface of the image pickup device 301.

Referring to FIG. 3, radioactive rays emitted from the radiation source 303 are transmitted through objects 302, images of which are to be picked up, and are modulated. The radiation intensity of each of the radioactive rays is detected on the radiation receiving surface of the image pickup device 301. The radiation receiving element outputs an electrical signal corresponding to the radiation intensity, and the image pickup device 301 performs predetermined processing for the electrical signal to generate rear-projected image data. The rear-projected image data captured by gradually moving the radiation source 303 is output as parallax image data corresponding to the position (radiation source position) of the radiation source 303.

Referring back to FIG. 2, the stereoscopic-image generating system also includes a stereoscopic-image processing unit 202. The stereoscopic-image processing unit 202 converts the parallax image data supplied from the radiation image pickup unit 201 into data appropriate for a stereoscopic image and transmits the converted data to a three-dimensional display 206 as an image signal or image data. The stereoscopic-image processing unit 202 also functions as a control device for the radiation image pickup unit 201 and, furthermore, calculates radiation source positions corresponding to control parameters described below. The stereoscopic-image processing unit 202 is, for example, a general-purpose engineering workstation or a personal computer.

The stereoscopic-image generating system further includes an input-output device 203. The input-output device 203 outputs the captured rear-projected image data and/or stereoscopic image data given by synthesizing the rear-projected image data and receives the rear-projected image data that has been previously captured. When information concerning the number of viewpoints and/or an estimated observation distance, which are three-dimensional display parameters as presentation parameters that are related to the three-dimensional display and are specific to the three-dimensional display 206, is to be provided as file data, the file data is input through the input-output device 203. The input-output device 203 reads and writes data recorded on a fixed recording media, such as a floppy disk, a magneto-optical disk (MO), an Iomega Zip®, a compact disk read only memory (CD-ROM), a CompactFlash® card, or a Smartmedia® card.

The input-output device 203 may be a network port, such as an Ethernet®, connected to a network. Or, the input-output device 203 may include an antenna, a receiver, and a transmitter for wireless communication. In such cases, the data concerning the rear-projected image and the three-dimensional display parameters is captured over the network.

The input-output device 203 includes a cable connected thereto to transmit an image signal to the three-dimensional display 206. The input-output device 203 may include a data bus used for extracting the three-dimensional display parameters from the firmware of the three-dimensional display 206.

The stereoscopic-image generating system further includes an operation display 204, which is the display unit for the stereoscopic-image processing unit 202. A photographer or an observer interactively inputs information required for stereoscopic image conversion or stereoscopic image display with the operation display 204. The operation display 204 assists the stereoscopic-image processing unit 202 to acquire such information. The operation display 204 also displays the processing status in the stereoscopic-image processing unit 202 or an operation menu, displays a group of large parallax images resulting from the image conversion, and displays the stereoscopic images by time-division multiplexing. The operation display 204 is a general display using, for example, a cathode ray tube (CRT) or a liquid crystal panel.

The stereoscopic-image generating system further includes an input device 205, such as a mouse, a keyboard, or a joystick. The photographer or observer selects an item from the operation menu or inputs data with the input device 205 while observing the menu displayed in the operation display 204. When the operation display 204 is a touch panel, the operation display 204 also serves as the input device 205.

The three-dimensional display 206 serving as a presentation device displays a stereoscopic image (a group of parallax images) after the stereoscopic image conversion by the stereoscopic-image processing unit 202. The three-dimensional display 206 is dedicated to the three-dimensional display and uses a light-ray-direction control member, such as a parallax barrier or a lenticular lens array, directing a light ray from each parallax image to a predetermined observation position (viewpoint).

When either a two-dimensional display function or a three-dimensional display function can be selected, as in a display disclosed in Japanese Patent Laid-Open No. 10-232665, the three-dimensional display 206 also serves as the operation display 204. In such a case, the two-dimensional function or the three-dimensional function can arbitrarily and selectively used. For example, only the stereoscopic images are three-dimensionally displayed and images other than the stereoscopic images are two-dimensionally displayed.

The stereoscopic-image generating system further includes a printer 207 serving as a presentation device. The printer 207 prints the stereoscopic image subjected to the stereoscopic image conversion and synthesis in the stereoscopic-image processing unit 202. The printer 207 is not limited to a general-purpose printer that prints the data on a normal recording medium, such as a paper sheet or a film. The printer 207 may be a printer that prints data on a polarizing element, such as a lenticular sheet or an integral sheet, for displaying the stereoscopic image or may be a printer, such as a holographic stereogram printer, for three-dimensional printing, which printer converts the input large parallax image into hologram information and prints the three-dimensional information.

The printer 207 has three-dimensional printing parameters (presentation parameters) different from the three-dimensional display parameters of the three-dimensional display 206, with respect to the number of viewpoints and the estimated observation distance. In other words, the printer 207 converts and synthesizes the print data on the stereoscopic images by using the three-dimensional printing parameters different from the three-dimensional display parameters of the three-dimensional display 206.

The stereoscopic-image generating system further includes a database 208 on a network. The database 208 associates a data file including the large parallax images, which file serves as an input source, and presentation parameter data corresponding to the various presentation devices with keywords and stores the associated data file and presentation parameter data.

The internal structure of the stereoscopic-image processing unit 202 is described next. The stereoscopic-image processing unit 202 includes a central processing unit (CPU) 2021 controlling the stereoscopic-image processing unit 202.

The stereoscopic-image processing unit 202 also includes a mass storage device 2022. The mass storage device 2022 stores the group of the parallax images input through the input-output device 203 and/or stores the stereoscopic image data and so on converted from the group of the parallax images. It is preferable that the mass storage device 2022 be a fixed storage medium, such as hard disk. The mass storage device 2022 may store a database, including the three-dimensional display parameters.

The stereoscopic-image processing unit 202 further includes a main memory device 2023, such as a random access memory (RAM). The main memory device 2023 stores the input data concerning the large parallax images and the three-dimensional display parameters and/or temporarily stores the stereoscopic image data after the stereoscopic image conversion before the data is stored in the mass storage device 2022 or is output through the input-output device 203.

Figure 4:
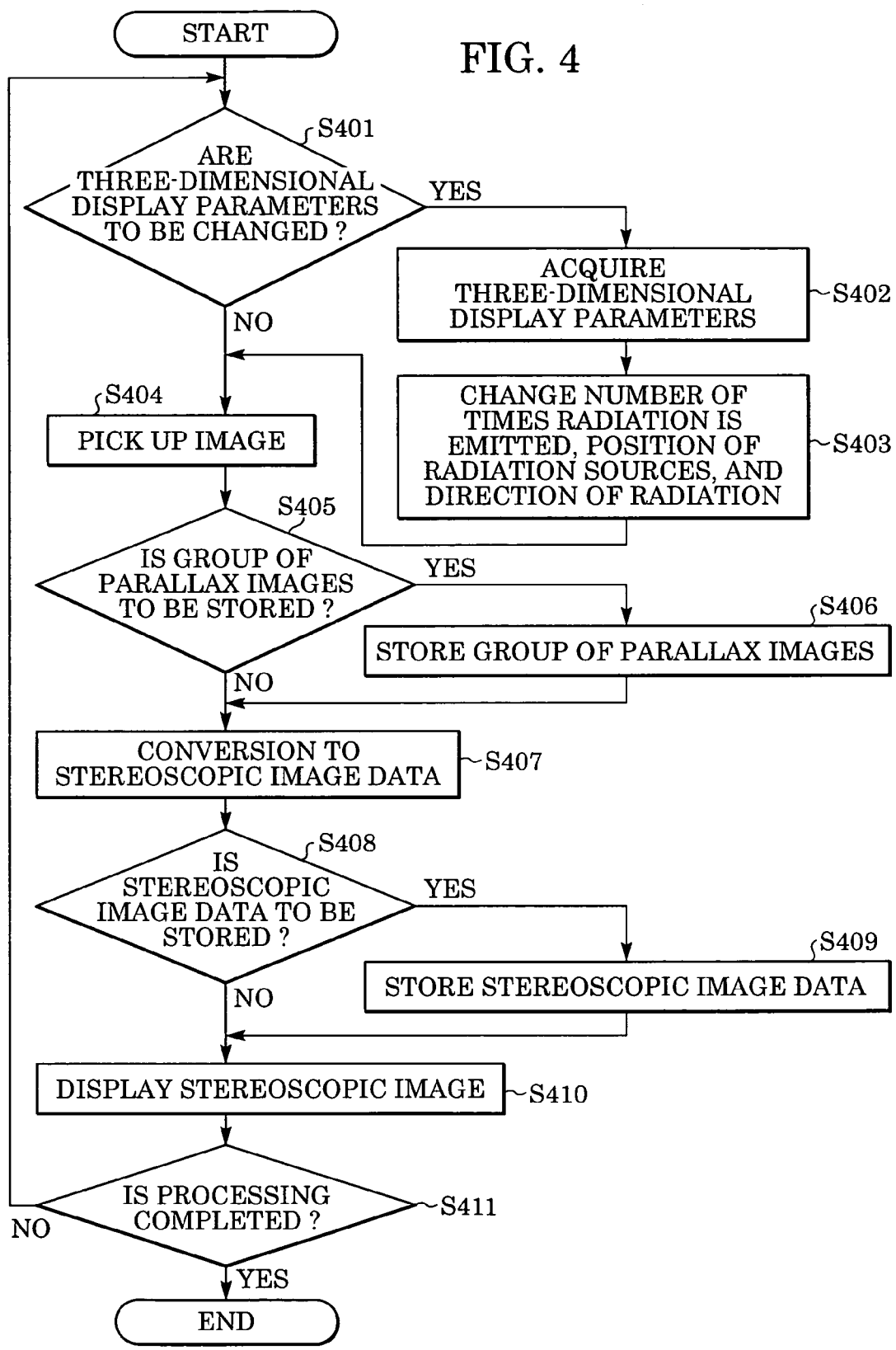
FIG. 4 is a flowchart showing the operation of the stereoscopic-image generating system according to the fist embodiment of the present invention.

FIG. 4 is a flowchart showing the operation of the stereoscopic-image generating system having the structure described above.

The stereoscopic-image generating system has a real-time mode and a storage-and-reproduction mode as stereoscopic image generating modes. In the real-time mode, the stereoscopic-image generating system picks up the rear-projected images (the group of parallax images) corresponding to the characteristics of the stereoscopic image to be displayed, generates the stereoscopic image data using the group of parallax images, and presents (displays or prints) the stereoscopic image. In the storage-and-reproduction mode, the stereoscopic-image generating system picks up and stores the rear-projected images corresponding to the positions of a predetermined number of radiation sources, selects a rear-projected image corresponding to the position of the radiation source, appropriate for the characteristics of the stereoscopic image to be reproduced, from among the stored images, and performs the conversion into the stereoscopic image by using the selected rear-projected image to present the stereoscopic image. When there is no rear-projected image corresponding to the position of the radiation source appropriate for the characteristics of the stereoscopic image to be reproduced in the stored images in the storage-and-reproduction mode, the stereoscopic-image generating system may generate a new rear-projected image based on the rear-projected image corresponding to the position of the radiation source appropriate for the characteristics of the stereoscopic image, and may perform the stereoscopic image conversion for the new rear-projected image.

The operation of the stereoscopic-image processing unit 202 (particularly of the CPU 2021), according to the first embodiment of the present invention, when the stereoscopic image is to be displayed mainly in the three-dimensional display 206 in the real-time mode is described next with reference to FIG. 4.

In Step S401, the CPU 2021 confirms whether the three-dimensional display parameters are to be changed. The three-dimensional display parameters are used for setting the number of times the radiation is emitted, the positions of (the interval between) the radiation sources, and the direction of radiation when the rear-projected images are picked up to display one or more stereoscopic images.

The three-dimensional display parameters include the number of viewpoints, the estimated observation distance, the angle of view, a binocular observation image step (an interval between binocular viewpoints), a display size, and a critical range of the three-dimensional effect, which are specific to the three-dimensional display 206. The three-dimensional display parameters also include a zoom ratio and a three-dimensional effect, which are appropriately adjusted in accordance with the preference of the observer watching the three-dimensional display 206. The three-dimensional display parameters further include the scope of the object.

The CPU 2021 acquires these three-dimensional display parameters by reading the values input by the observer with the input device 205 or by reading a file including the three-dimensional display parameters through the input-output device 203. The observer inputs the values while referring to the values displayed on the console of the operation display 204 or while observing the stereoscopic image displayed in the three-dimensional display 206.

The three-dimensional display parameters may be expanded in the main memory device 2023 in the stereoscopic-image processing unit 202 in order to allow rapid acquisition of the three-dimensional display parameters during the pickup or to allow rapid update of the three-dimensional display parameters.

Main parameters among the three-dimensional display parameters are described next.

The number of viewpoints of the three-dimensional display 206 means the maximum number of kinds of images capable of being observed in the three-dimensional display 206 when an observer's eyes are placed at positions appropriate for the observation, and corresponds to the number of parallax images to be picked up. The observer observes two parallax images having a parallax therebetween to observe one stereoscopic image.

The estimated observation distance means a distance between the three-dimensional display 206 and the viewpoints, which distance is estimated in the three-dimensional display 206 and is appropriate for the observation of the stereoscopic image. The estimated observation distance is a design parameter of the three-dimensional display 206 and ordinarily varies with the kind of the three-dimensional display 206. For example, the interval between the viewpoints is optimized so as to provide a most superior stereoscopic image at the estimated observation distance.

The angle of view means a ratio of the size of the display surface of the three-dimensional display 206 to the estimated observation distance.

Figure 5A:
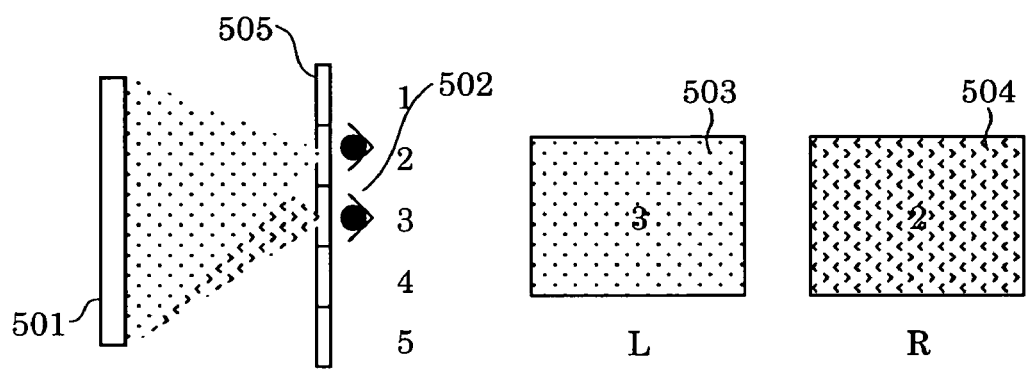
FIGS. 5A and 5B show examples of parallax images observed when two three-dimensional displays having different presentation parameters are used, according to the first embodiment of the present invention.
Figure 5B:
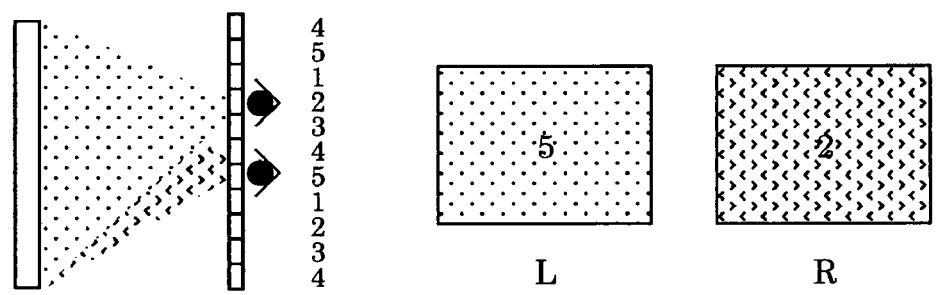

The binocular observation image step means a distance between the two parallax images observed by the observer's left and right eyes. FIGS. 5A and 5B show two three-dimensional displays which have the same estimated observation distance but differ from each other in the interval between the viewpoints. The number of viewpoints of the three-dimensional display 206 in FIG. 5B is larger than that of the three-dimensional display in FIG. 5A. Accordingly, the observer has a narrower field of view in FIG. 5B, compared with the case in the three-dimensional display in FIG. 5A.

The three-dimensional display 206 according to the first embodiment realizes the observation of the stereoscopic image from three or more viewpoints by horizontally (in some cases, horizontally and vertically) displaying in parallel three or more parallax images, picked up with the baseline lengths being set to equal. The number of parallax images corresponds to the number of viewpoints specific to the three-dimensional display 206. Since light rays from the same parallax image are led to a plurality of viewpoints in the three-dimensional display in FIG. 5B, a plurality of observers can simultaneously observe the same stereoscopic image.

In the three-dimensional displays shown in FIGS. 5A and 5B, reference numeral 501 denotes the display surface of the three-dimensional display and reference numeral 502 denotes the observer's eyes. Reference numeral 505 denotes viewpoints, which are actually transparent. Reference numerals from 1 to 5 on the right side of the viewpoints 505 denote viewpoint numbers. The light rays from the same parallax image are led to the viewpoints having the same number.

Reference numeral 503 denotes a parallax image observed by the left eye (L) (the parallax image corresponding to the viewpoint 3 in FIG. 5A and the parallax image corresponding to the viewpoint 5 in FIG. 5B), and reference numeral 504 denotes a parallax image observed by the right eye (R) (the parallax image corresponding to the viewpoint 2 both in FIGS. 5A and 5B).

In the three-dimensional display 206 in FIG. 5A, the parallax images corresponding to the two adjoining viewpoints, among the five viewpoints from the viewpoint 1 to the viewpoint 5, are observed by the left and right eyes. In contrast, the three-dimensional display 206 in FIG. 5B circularly presents the five parallax images corresponding to the view point 1, the viewpoint 2, . . . , the viewpoint 5 and, therefore, has a narrower separation width of the viewpoints (a narrower interval between the viewpoints), compared with the three-dimensional display in FIG. 5A. Hence, the parallax images corresponding to two viewpoints spaced two viewpoints apart are observed by the left and right eyes of the observer. For example, the parallax image observed by the left eye corresponds to the viewpoint 2 and the parallax image observed by the right eye corresponds to the viewpoint 5. In other words, the relationship of the parallax between the parallax images observed by the left and right eyes at a predetermined observation distance is referred to as the binocular observation image step.

When the group of parallax images picked up with the same baseline length as in FIG. 5A being set is displayed in the three-dimensional display in FIG. 5B, the baseline length between the parallax images observed by the left and right eyes is three times larger than that in FIG. 5A, so that the three-dimensional display in FIG. 5B exhibits a stereoscopic view having the amount of floating and the amount of sinking three times larger than that in FIG. 5A. Accordingly, observing the stereoscopic image resulting from the same group of parallax images at the same geometrical position does not provide the same stereoscopic view. In order to achieve the same stereoscopic view, it is necessary to display, or pick up the images in consideration of the binocular observation image step. The binocular observation image step is also a design parameter of the three-dimensional display and ordinarily varies with the kind of the three-dimensional display.

When the three-dimensional display is based on, for example, a lenticular technology or an integral photography, any variation in the observation distance or in the spatial positions of the observer's eyes with respect to the display surface varies the binocular observation image step. In such a case, the binocular observation image step is given as a function or a table having the coordinate parameters of the positions of the observer's eyes as arguments in order to support big variations in the positions of the observer's eyes. As a result, an eye coordinate parameter is provided as a secondary parameter for setting the binocular observation image step. In this case, as disclosed in Japanese Patent Laid-Open No. 2-50145, the eye coordinates may be sequentially determined by using a head-position detection system or a vision sensor in which an azimuth sensor is combined with a magnetic sensor to calculate and update the binocular observation image step in real time.

The display size is an index indicating the size of the stereoscopic image displayed on the display surface of the three-dimensional display 206 or indicating the display range in a direction horizontal to the display surface of the stereoscopic image.

The critical range of the three-dimensional effect means the maximum value of the parallax capable of being presented on the display surface. That is, the critical range of the three-dimensional effect means the maximum amount of sinking and the maximum amount of floating of the stereoscopic image with respect to the display surface.

Originally, the parallax between the parallax images should be restricted by a fusion limit of a human being. However, when the three-dimensional display is used, the critical range of the three-dimensional effect is often and actually limited to a range narrower than the fusion limit of the human being due to, for example, crosstalk between the adjoining images. The critical range of the three-dimensional effect, which is dependent on the device, depends on the design parameter of the three-dimensional display or the method of emitting the light rays adopted in the three-dimensional display, and ordinarily varies with the kind of the three-dimensional display. Accordingly, the critical range of the three-dimensional effect is acquired from experiment data or an evaluation result yielded by the observation of the stereoscopic image.

As described above, the binocular observation image step varies with the kind of the three-dimensional display or with the observation position. For example, when the critical range of the three-dimensional effect is represented on the basis of the parallax between the parallax images adjacently presented at the observation position, the double binocular observation image step halves the parallax restricted by the fusion limit of the human being. In contrast, the parallax restricted by the critical range of the three-dimensional effect, which is dependent on the device, remains unchanged.

When the binocular observation image step varies, the parallax restricted by the critical range of the three-dimensional effect, which is dependent on the device, can have a maximum value larger than that of the parallax restricted by the fusion limit. In such a case, for example, the parallax restricted by the fusion limit of the human being is compared with the parallax restricted by the critical range of the three-dimensional effect, which is dependent on the device, with respect to the parallax between the parallax images adjacently presented at the observation position. The critical range of the three-dimensional effect is limited to a smaller parallax, among the parallax restricted by the fusion limit of the human being and the parallax restricted by the critical range of the three-dimensional effect, which parallax being measured between points in the presented parallax images.

The zoom ratio means the magnification of a zoom function for enlarging part of the stereoscopic image. For example, the observer selects an area in the stereoscopic image by using a user interface to enlarge the area with the zoom function and to display the enlarged area.

The three-dimensional effect is a parameter indicating how much the stereoscopic view is adjusted. Adjusting the three-dimensional effect allows the stereoscopic view to be increased or decreased. When the three-dimensional display presents only the horizontal parallax, the parallax images forming the stereoscopic image are horizontally shifted by adjusting the three-dimensional effect to vary the balance between the floating and the sinking.

In order to increase the level of the stereoscopic view, or the parallax between the parallax images, the images are picked up with a larger baseline length being set. Contrarily, in order to decrease the stereoscopic view, the images are picked up with a smaller baseline length being set. In order to present the natural stereoscopic view that faithfully reflects the display scale, the three-dimensional effect is ignored. When the parallax between the parallax images after the adjustment exceeds the critical range of the three-dimensional effect, either the stereoscopic view or the critical range of the three-dimensional effect is given priority over the other to adjust the three-dimensional effect. When the critical range of the three-dimensional effect is given priority over the stereoscopic view, the parallax is adjusted or the balance between the floating and the sinking is adjusted such that the critical range of the three-dimensional effect is within the display range of the three-dimensional display.

When the three-dimensional display parameters are varied due to the replacement of the three-dimensional display 206, the movement of the enlarged area, the change in the zoom ratio, the adjustment of the three-dimensional effect, etc., the CPU 2021 acquires the up-to-date three-dimensional display parameters for update.

The scope of the object means the scope of the object 302 arranged between the radiation source 303 and the radiation receiving surface of the image pickup device 301, shown in FIG. 3, in a direction extending from the radiation source 303 to the radiation receiving surface. This parameter is set by the observer who inputs an approximate value or detects an area occupied by the object with the vision sensor. The scope of the object is important in presenting an eye-friendly stereoscopic image when the stereoscopic image having a large parallax is displayed in a three-dimensional display having a very narrow critical range of the three-dimensional effect.

When the three-dimensional display parameters described above are varied, the CPU 2021 performs Steps S402 and S403 in FIG. 4 because the number of the radiation sources 303 (the number of times the radiation is emitted), the positions of (the interval between) the radiation sources, and the direction of radiation must be changed.

Referring back to FIG. 4, in Step S402, the CPU 2021 acquires the three-dimensional display parameters from the inputs with the input device 205 in a graphical user interface (GUI) displayed in the operation display 204 or the three-dimensional display 206 or acquires the three-dimensional display parameters by reading the data file through the input-output device 203. Among the three-dimensional display parameters, a gradually varying parameter, for example, the scope of a moving object is acquired by using a sensor for monitoring the displacement of the object between the radiation sources and the image pickup device.

If no three-dimensional display parameter is acquired (the first routine immediately after the startup), the CPU 2021 acquires all the three-dimensional display parameters. In the second and subsequent routines, only the parameters the change of which is confirmed in Step S401 are acquired for update.

After acquiring the up-to-data three-dimensional display parameters, the CPU 2021 sets the conditions for picking up the parallax images in the following steps in order to generate the stereoscopic image having an appropriate stereoscopic view.

In Step S403, the CPU 2021 changes the positions of the radiation sources and the direction of radiation. The CPU 2021 calculates the number of times the radiation is emitted, the positions of (the interval between) the radiation sources, and the direction of radiation, when a plurality of parallax images are picked up, based on the three-dimensional display parameters acquired in Step S402.

A method of determining the positions of the radiation sources and the direction of radiation based on the three-dimensional display parameters is described next.

First, the number of the radiation sources (the number of times the radiation is emitted) is determined based on the number of viewpoints. Next, two radiation sources forming the parallax image (rear-projected image) observed by the observer's left and right eyes at the estimated observation distance are estimated, and the interval between the two radiation sources (the relative position in the direction of movement of the radiation sources among the relative positions between the radiation sources and the image pickup device) is determined. This interval between the two radiation sources is determined in accordance with the binocular observation image step. The interval between all the radiation sources is determined based on this interval between the two radiation sources.

Then, the distance between the radiation sources and the radiation receiving surface (that is, the relative position in the direction of projecting the image among the relative positions between the radiation sources and the image pickup device) and the size of the radiation receiving surface are adjusted based on the estimated observation distance and the display size. The size of the radiation receiving surface means the size of a radiation receiving area, on the radiation receiving surface, corresponding to the field of view of the image displayed in the three-dimensional display. The size of the radiation receiving surface also varies with a variation in the zoom ratio. The picked-up parallax image may be expanded or reduced, instead of varying the size of the radiation receiving surface.

In order to display the stereoscopic image having natural stereoscopic view, the distance between the radiation sources and the radiation receiving surface and the size of the radiation receiving surface are adjusted so as to satisfy Formula 1.

[Formula 1]

$$\frac{\text{Observed baseline length}}{\text{Interval between radiation sources}} \times \frac{\text{Estimated observation distance}}{\text{Distance between radiation sources and radiation receiving surface}} \times \frac{\text{Size of radiation receiving surface}}{\text{Size of display surface}} = 1$$

When the interval between the positions of the radiation source is determined in consideration of the three-dimensional effect and the critical range of the three-dimensional effect, the interval between the positions of the radiation source is calculated so as to satisfy Formula 2.

[Formula 2]

$$\frac{\text{Observed baseline length}}{\text{Interval between radiation sources}} \times \frac{\text{Estimated observation distance}}{\text{Distance between radiation sources and radiation receiving surface}} \times$$

$$\frac{\text{Size of radiation receiving surface}}{\text{Size of display surface}} \times \text{Coefficient of three-dimensional effect} = 1$$

When the critical range of the three-dimensional effect is not considered, the coefficient of the three-dimensional effect means a coefficient representing the three-dimensional effect parameter. When the coefficient of the three-dimensional effect is equal to one, the stereoscopic image exhibits the natural stereoscopic view. On the conditions that the same estimated observation distance and the same display size are used and that the distance between the radiation sources and the radiation receiving surface and the size of the radiation receiving surface are not varied, when the coefficient of the three-dimensional effect is larger than one, the interval between the positions of the radiation source is reduced and the stereoscopic view is decreased so as to reduce the parallax. On the above conditions, when the coefficient of the three-dimensional effect is smaller than one, the stereoscopic view is increased.

In contrast, when the critical range of the three-dimensional effect is considered, the interval between the positions of the radiation source is calculated so as not to exceed the critical range of the three-dimensional effect, that is, not to exceed the parallax limit within which the stereoscopic image can be presented on the three-dimensional display. Since known three-dimensional displays have a very narrower critical range of the three-dimensional effect, compared with the parallax restricted by the fusion limit of a human being, the interval between the positions of the radiation source, that is, the stereoscopic view of the displayed stereoscopic image, is often restricted by the critical range of the three-dimensional effect.

When a coefficient for considering the critical range of the three-dimensional effect is referred to as a three-dimensional effect restriction coefficient, Formula 3 is satisfied.

[Formula 3]

$$\frac{\text{Observed baseline length}}{\text{Interval between radiation sources}} \times$$

$$\frac{\text{Estimated observation distance}}{\text{Distance between radiation sources and radiation receiving surface}} \times \frac{\text{Size of radiation receiving surface}}{\text{Size of display surface}} \times$$

$$\text{Coefficient of three-dimensional effect} \times \text{Three-dimensional effect restriction coefficient} = 1$$

The three-dimensional effect restriction coefficient is calculated in consideration of the scope of the object, in addition to the three-dimensional display parameters used in the interval between the positions of the radiation source.

The critical range of the three-dimensional effect primarily sets the parallax on the display surface, corresponding to the maximum amount of floating and the maximum amount of sinking which can be presented in the three-dimensional display. When the critical range of the three-dimensional effect is equal to the parallax between the adjoining parallax images forming the stereoscopic image that presents the maximum amount of floating and the maximum amount of sinking, the critical range of the three-dimensional effect is converted into the value corresponding to the binocular observation image step at the estimated observation distance by using the binocular observation image step, the display size, and the size of the radiation receiving surface. Alternatively, the critical range of the three-dimensional effect is converted into the value of the parallax between parallax images formed by the estimated two radiation sources.

The three-dimensional effect restriction coefficient is set by using the distance between the radiation sources and the radiation receiving surface, the size of the radiation receiving surface, and the interval between the positions of the radiation source, which are calculated in consideration of the three-dimensional effect parameters, such that the parallax calculated for the scope of the object or the parallax between the parallax images determined by the positions of the radiation sources does not exceed the parallax set above.

Figure 7:
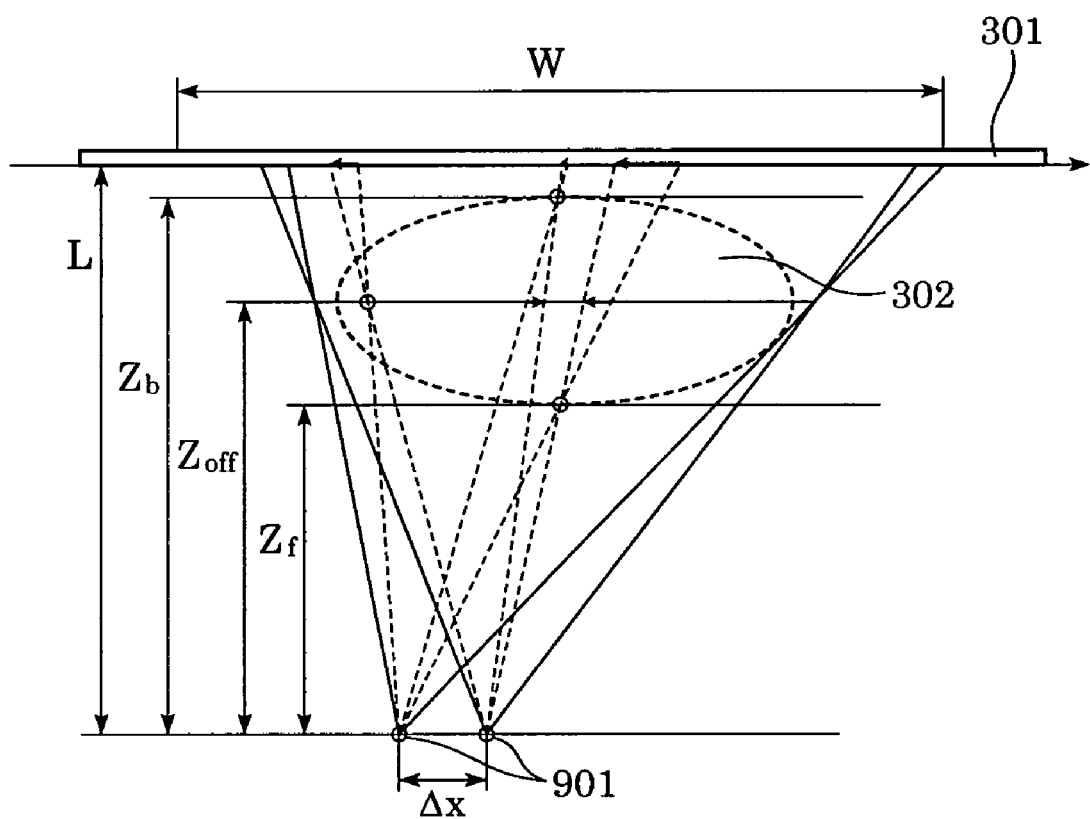
FIG. 7 illustrates the relationship between an image pickup device and parallax.

The parallax is calculated in the following manner. FIG. 7 illustrates the parallax on a radiation receiving surface 301, yielded when an image of an object 302 is picked up with an image pickup device. Two estimated radiation sources 901, the radiation receiving surface 301, and the object 302 are shown in FIG. 7.

Parallax $\Delta d_L$ at a distance L between the radiation sources and the radiation receiving surface is calculated by using Formula 4. In Formula 4, Z denotes a vertical distance between a spatial point of the object and the radiation receiving surface.

[Formula 4]

$$\Delta d_L(Z) = \left(\frac{L}{Z} - 1\right)\Delta x$$

The parallax $\Delta d_L$ is determined from the geometrical relationship among an interval $\Delta x$ between the radiation sources 901, a distance L between the radiation sources 901 and the radiation receiving surface 301, and the distance Z between the spatial point and the radiation receiving surface 301.

The size of the radiation receiving surface is different from the size of the actual radiation receiving element, as described above.

The range of the parallax calculated for the scope of the object can be varied by adjusting the relationship between the distance between the radiation sources and the radiation receiving surface and the size of the radiation receiving surface by image shift and variable magnification processing. The parallax between the parallax images, yielded when a virtual radiation receiving surface is provided at a distance $Z_{off}$ from the radiation sources 901, is given by Formula 5.

[Formula 5]

$$\Delta d_{Z_{off}}(Z) = \left(\frac{Z_{off}}{Z} - 1\right)\Delta x = \left(\frac{Z_{off} - Z}{Z}\right)\Delta x$$

A parallax $\Delta d'$ between the images, given by shifting the parallax images so as to set a parallax $\Delta d_L(Z_{off})$ on the radiation receiving surface at the distance L, corresponding to the spatial point at the distance $Z_{off}$ from the radiation sources 901, to zero and by calculating the variable power of $Z_{off}/L$, is calculated by using Formula 6.

[Formula 6]

$$\Delta d'(Z) = \frac{Z_{off}}{L}\{\Delta d_L(Z) - \Delta d_L(Z_{off})\}$$
$$= \frac{Z_{off}}{L}\left\{\left(\frac{L}{Z} - 1\right)\Delta x - \left(\frac{L}{Z_{off}} - 1\right)\Delta\right\}x$$
$$= \frac{(Z_{off} - Z)}{Z}\Delta x$$

In other words, performing the image shift and the variable magnification processing for the image provides the parallax between the parallax images when the relationship between the distance between the radiation sources and the radiation receiving surface and the size of the radiation receiving surface is varied. This processing is useful for efficiently restricting the range of the parallax within the critical range of the three-dimensional effect.

Next, the intervals between all the radiation sources are determined. An equal interval between the positions of the radiation source is calculated based on the relationship between the interval between the two radiation sources corresponding to the two parallax images observed by the observer's left and right eyes at the estimated observation distance and the binocular observation image step of the two parallax images observed by the observer's left and right eyes at the estimated observation distance. All the radiation sources are ordinarily arranged at an equal distance from each other. However, in the case of the three-dimensional display imitating convergence, an unequal distance is calculated and set in consideration of the geometrical relationship.

Finally, the direction of radiation is determined. The object is efficiently irradiated with radiation rays in accordance with the variation in the positions of the radiation sources to determine the direction of radiation so as to receive the radiation rays on the radiation receiving surface. In order to efficiently obtain a projected image, the radiation receiving surface may be horizontally shifted with respect to the object in accordance with the positions to which the radiation sources move and the direction of radiation.

In addition, in order to efficiently pick up all the parallax images of the object, the direction of radiation may be set such that the central axis of the direction of radiation intersects with the target position of the object, and the radiation receiving surface may be shifted so as to efficiently receive the transmitted radiation rays.

A specific example of an adjustment method to accomplish similar stereoscopic view in three-dimensional displays having different binocular observation image steps at the estimated observation distance is described next with reference to FIGS. 5A and 5B.

In the adjustment of the stereoscopic view, the interval between the positions of the radiation source is adjusted as shown in FIGS. 1A and 1B. Referring to FIGS. 1A and 1B, a three-dimensional display 101 corresponds to FIG. 5A, and a three-dimensional display 102 corresponds to FIG. 5B. The three-dimensional displays 101 and 102 have the same estimated observation distance but differ in the binocular observation image step.

A predetermined number of parallax images are picked up at positions 103 of the radiation sources. The number of the parallax images corresponds to the number of viewpoints of the three-dimensional displays 101 and 102. Two positions 104 of the radiation sources, indicated by solid lines, represent the positions of the radiation sources when the two parallax images forming one stereoscopic image are picked up, as shown in FIGS. 5A and 5B. Reference numeral 106 denotes an image pickup device (the radiation receiving surface). Reference numeral 105 denotes objects.

In order to accomplish similar stereoscopic view at the same estimated observation distance in the three-dimensional displays having different binocular observation image steps, the positions of the radiation sources (the interval between the positions of the radiation source) are adjusted such that the baseline length when the two parallax images observed by the observer's left and right eyes at the estimated observation distance are picked up, as shown in FIG. 1B, becomes equal to the baseline length when the two parallax images are picked up, as shown in FIG. 1A. That is, the radiation sources are moved so as to provide the same parallax between the two parallax images simultaneously observed by the left and right eyes of the observer in both the three-dimensional displays.

The positions of the radiation sources (the interval between the positions of the radiation source) are similarly adjusted when the overall stereoscopic view (that is, the level of the stereoscopic view, or the amount of floating in the display of the stereoscopic image) is varied.

As described above, even when different three-dimensional displays are used, it is possible to automatically present the stereoscopic images in the same stereoscopic view by adjusting the positions of the radiation sources and the direction of radiation based on the three-dimensional display parameters of the three-dimensional displays, that is, by adjusting and controlling the relative positions of the radiation sources and the image pickup device.

Figure 6A:
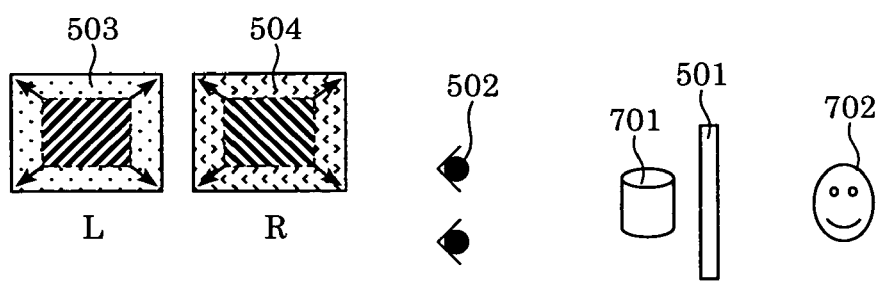
FIGS. 6A to 6C illustrate variations in stereoscopic views due to enlargement of part of images according to the first embodiment of the present invention.

A case in which the positions of the radiation sources are varied with a variation in the zoom ratio is described next with reference to FIGS. 6A to 6C. Referring to FIG. 6A, reference numeral 501 denotes the display surface of a three-dimensional display, reference numeral 502 denotes the eyes of an observer, reference numeral 503 denotes the parallax image observed by the observer's left eye (L), and reference numeral 504 denotes the parallax image observed by the observer's right eye (R).

Reference numeral 701 denotes a stereoscopic image floating with respect to the display surface 501 of the three-dimensional display, recognized by the observer who observes the parallax images 503 and 504. Reference numeral 702 denotes a stereoscopic image sinking with respect to the display surface 501 of the three-dimensional display. First, it is presumed that the floating stereoscopic image 701 and the sinking stereoscopic image 702 appear in the positions in FIG. 6A with respect to the display surface 501 of the three-dimensional display when the observer observes the stereoscopic image at certain viewpoints. Next, part of the parallax image is enlarged without changing the viewpoints. Shaded areas in the parallax images 503 and 504 in FIG. 6A are to be enlarged.

Figure 6B:
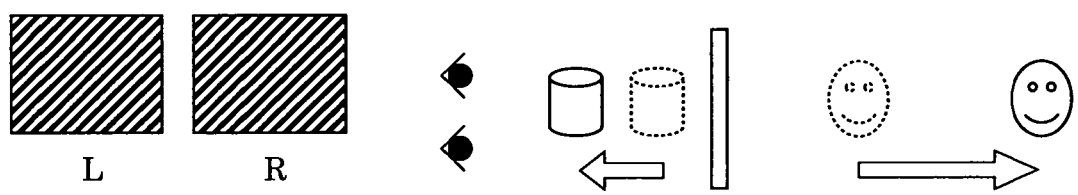
Figure 6C:
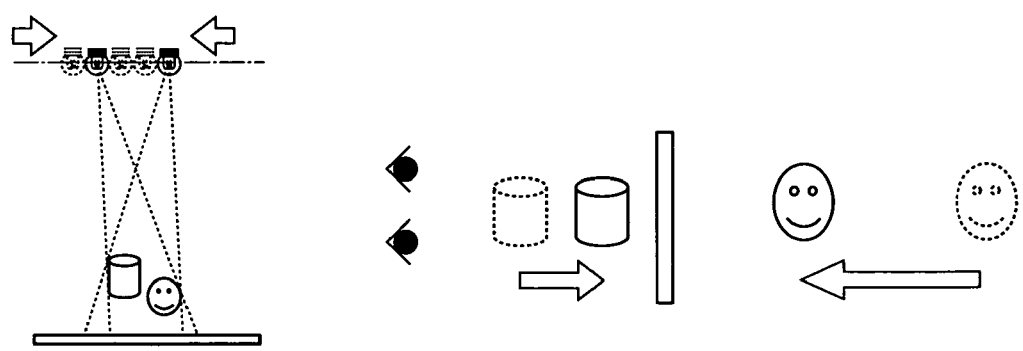

When the shaded areas are enlarged in the display surface 501 of the three-dimensional display, the parallax between the points corresponding to the shaded areas in the parallax images 503 and 504 is varied, as shown in FIG. 6B. Since the parallax is increased in the enlargement, the amount of floating and the amount of sinking with respect to the display surface 501 of the three-dimensional display are increased. When the amount of floating and the amount of sinking are excessively increased, they exceed the fusion limit of the observer or the critical range of the three-dimensional effect of the three-dimensional display. In such a case, the amount of floating and the amount of sinking with respect to the display surface 501 of the three-dimensional display are suppressed by decreasing the interval between the positions of the radiation source when the parallax images 503 and 504 after the enlargement are picked up, as shown in FIG. 6C.

Referring back to FIG. 4, in Step S404, the CPU 2021 picks up a rear-projected image. Specifically, the CPU 2021 causes the radiation sources to emit the radiation rays in the directions of radiation determined at the positions of the radiation sources while causing the radiation sources to sequentially move to the positions determined based on the three-dimensional display parameters, and sequentially picks up a plurality of rear-projected images (a group of parallax images) of an object with the image pickup device 301. In the pickup of the rear-projected images in Step S404, basic image processing, such as tone conversion and sharpening, is performed for the picked-up images.

In Step S405, the CPU 2021 confirms whether the group of parallax images picked up in Step S404 is to be stored in the mass storage device 2022. Specifically, the CPU 2021 displays a menu in the operation display 204, from which menu the observer makes a choice. If the group of parallax images is to be stored, in Step S406, the CPU 2021 stores the group of parallax images in the mass storage device 2022.

The group of parallax images stored in Step S406 is, for example, used for generating stereoscopic image data in another processing apparatus, is individually read out and observed as a two-dimensional rear-projected image, or used for the purpose of generating an arbitrary viewpoint image described below.

In Step S407, the CPU 2021 performs conversion to stereoscopic image data. The CPU 2021 synthesizes the group of parallax images, picked up in Step S404, in accordance with the pixel array in the three-dimensional display to generate the stereoscopic image data. Specifically, the CPU 2021 generates the stereoscopic image data by multiplexing in which pixel information is sampled from each parallax image and the pixel information is synthesized.

Multiplex processing for reproducing a stereoscopic image from a group of parallax images and displaying the reproduced stereoscopic image in a display adopting a light-ray reproduction method is disclosed in, for example, Japanese Patent Laid-Open No. 2002-171536. Multiplex processing using a light-ray-direction control member, such as a lenticular sheet or parallax barrier, is disclosed in, for example, Japanese Patent Laid-Open No. 2003-209858. The stereoscopic image data may be generated in such multiplex processing.

In Step S408, the CPU 2021 confirms whether the stereoscopic image data generated in Step S407 is to be stored in the mass storage device 2022 in the same manner as in Step S405. Storing the stereoscopic image data in the mass storage device 2022 allows the stereoscopic image data to be read out later to display the stereoscopic image without taking the image. If the stereoscopic image data is to be stored, in Step S409, the CPU 2021 stores the stereoscopic image data in the mass storage device 2022.

In Step S410, the CPU 2021 outputs the stereoscopic image data yielded by the conversion to the stereoscopic image data in Step S407 to the three-dimensional display 206 and displays the stereoscopic image.

In the display in Step S410, the stereoscopic image data may be output on the printer 207, instead of displaying the stereoscopic image in the three-dimensional display 206. When the stereoscopic image data is output on the printer 207, both in the case of directly printing the stereoscopic image data on an optical material, such as a lenticular sheet or an integral sheet, and in the case of printing the stereoscopic image data on a recording medium having such optical materials combined therein, it is preferable to perform the processing in Step S401 and subsequent steps again in order to generate stereoscopic image data appropriate for the print parameters of the optical material. Performing the processing from the beginning provides a superior stereoscopic image, compared with a case in which the stereoscopic image data generated in accordance with the three-dimensional display parameters of the three-dimensional display is printed.

In Step S411, the CPU 2021 determines whether the processing is completed. If a rear-projected image is to be picked up and a stereoscopic image is to be displayed again, the CPU 2021 returns to Step S401. If the pickup and display is not to be performed, the processing is completed.

Second Embodiment

A stereoscopic-image generating system according to a second embodiment of the present invention is described next. The stereoscopic-image generating system according to the second embodiment has the same structure as the stereoscopic-image generating system according to the first embodiment. The same reference numerals are used in the second embodiment to identify the same components in the first embodiment. A detailed description of such components is omitted herein.

According to the second embodiment, the storage-and-reproduction mode is described. In the storage-and-reproduction mode, a predetermined number of rear-projected images (the group of parallax images) are picked up and stored while varying the positions of the radiation source. Next, necessary parallax images are selected from the stored data based on the three-dimensional display parameters relating to the characteristics, including virtual positions of the radiation source (hereinafter referred to as virtual radiation source positions) corresponding to the stereoscopic image to be presented, the field of view, and the stereoscopic view, and the selected group of parallax images is converted into stereoscopic image data to display the stereoscopic image.

Specifically, in the storage-and-reproduction mode, a predetermined number of parallax images are picked up, the data concerning the parallax images are stored, and the stored data is used to generate a plurality of parallax images at arbitrary positions of the radiation source, corresponding to the virtual radiation source positions (hereinafter referred to as arbitrary viewpoint images) after the completion of the image pickup. Then, the arbitrary viewpoint images are converted into a stereoscopic image that is displayed. The arbitrary viewpoint images mean rear-projected images yielded when the radiation source and the radiation receiving surface are arranged at arbitrary positions.

It is possible in the storage-and-reproduction mode to efficiently pick up the rear-projected images, while considering a variation in quality level of the generated images due to the effect of the density of ray space data described below and of interpolation error to ensure the presentation of the stereoscopic image having a quality level higher than a predetermined level.

Figure 8B:
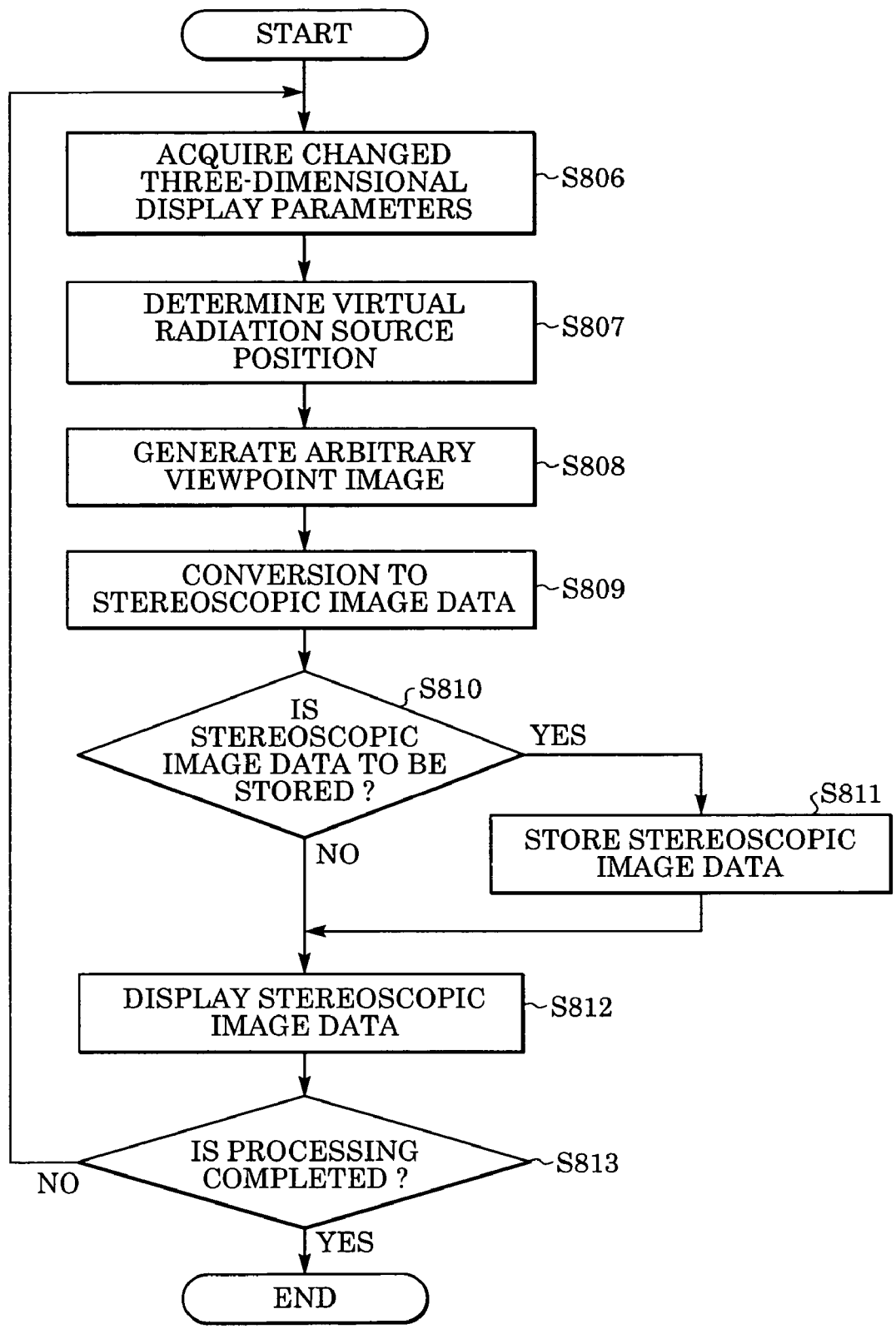

FIGS. 8A and 8B are flowcharts showing the operation of the stereoscopic-image processing unit 202 (particularly of the CPU 2021), according to the second embodiment of the present invention, when the stereoscopic image is to be displayed mainly in the three-dimensional display 206 in the storage-and-reproduction mode.

According to the second embodiment, the parallax images at a predetermined number of positions of the radiation source are picked up with the image pickup device 301 in the radiation image pickup unit 201, and the parallax images are stored in the mass storage device 2022 or the database 208 on the network or are stored in an external storage device through the input-output device 203. After the predetermined number of parallax images is picked up, the pickup of the parallax images is completed. This processing is referred to as an image-pickup and storage process.

Next, a plurality of arbitrary positions of the radiation source (virtual radiation source positions) corresponding to the stereoscopic image to be presented is determined to generate a plurality of arbitrary viewpoint images corresponding to the virtual radiation source positions. The stereoscopic image is generated and the stereoscopic image at the arbitrary viewpoints is displayed. This processing is referred to as a stereoscopic-image generation and display process.

FIG. 8A is a flowchart showing the operation in the image-pickup and storage process.

In Step S801, the CPU 2021 determines an allowable movement range of the viewpoint. Specifically, the CPU 2021 acquires information concerning the allowable range of the viewpoint positions that is allowed in the stereoscopic-image generation and display process at arbitrary positions, described below. When information concerning the resolution and the focal length of the image pickup device 301, the scope of the object, and a maximum texture resolution of the object has not been acquired, the CPU 2021 acquires such information by ray interpolation used in the generation of the arbitrary viewpoint images. The CPU 2021 further sets the values of the resolution, the focal length (the angle of view), and an allowable amount of zoom when the stereoscopic image is displayed, in Step S801.

The allowable amount of zoom corresponds to an allowable amount of variation in the angle of view when the angle of view is varied with a variation in the distance between the virtual radiation source position and the radiation receiving surface in the generation of the arbitrary viewpoint images.

Among the above information or values, the values relating to the image pickup and display are directly acquired from the image pickup device 301 and the three-dimensional display 206, respectively. The values relating to the image pickup and display include the resolution and the focal length of the image pickup device 301 and the allowable range of parallax in the three-dimensional display 206. The scope of the object and the maximum texture resolution of the object are acquired with a sensor provided toward the position of the object in the radiation image pickup unit 201. The other information, including the allowable movement range of the viewpoint and values that cannot be acquired with the above devices, is interactively acquired from the GUI in the operation display 204, in which GUI the observer inputs data with the input device 205.

In Step S802, the CPU 2021 determines a quality level of the arbitrary viewpoint image to be generated later. According to the second embodiment, the arbitrary viewpoint image that has not been picked up (stored) in the image pickup process in S804 described below is generated by the ray interpolation. Hence, the quality level of the arbitrary viewpoint image to be generated is set to a value corresponding to the density of the ray space data in light field rendering. Varying the quality level of the arbitrary viewpoint image to be generated varies the minimum interval between the positions of the radiation source.

The generation of the arbitrary viewpoint image by the ray interpolation is briefly described next. First, ray information is captured with a two-dimensional or one-dimensional array in the image pickup device. The array in the image pickup device may be replaced with a device in which a single or a plurality of image pickup devices is sequentially moved to pick up images.

A plane on which the image pickup device is provided is called a camera plane. A position on the camera plane, where an image is picked up, is expressed by a coordinate (s, t). A uv image coordinate system is set on the image picked up at each position. Accordingly, each ray forming the picked-up image is uniquely defined by the four parameters (s, t, u, and v).

The image (u, v) picked up at the coordinate (s, t) is decomposed as light-ray data, which is stored in a light-ray database. Alternatively, the group of the picked-up images may be stored as image array data and the light-ray data may be sequentially fetched from the image in the extraction of the light-ray data.

The arbitrary viewpoint image is generated by setting a new virtual image pickup position at an arbitrary spatial position and sequentially reading out all the light-ray data passing through the pixels forming the arbitrary viewpoint image and the image pickup position from the four-dimensional storage space (s, t, u, v) of the light-ray data to yield the values of the pixels.

However, when the necessary ray does not exist and cannot be acquired from the light-ray data, the ray is acquired by the ray interpolation. For example, the values of pixels having the same vertical coordinate value $v_x$ in the image coordinate system and the horizontal coordinate values, for example, $u_{x-1}$ and $u_{x+1}$, which are adjacent to the position of the ray to be acquired, among the light-ray data concerning the image pickup position $(s_x, t_x)$ that is closest to the virtual image pickup position, are used to perform the ray interpolation. Alternatively, the values of pixels having the same horizontal coordinate value $u_x$ and the vertical coordinate values, for example, $v_{x-1}$ and $v_{x+1}$, which are adjacent to the position of the ray to be acquired, may be used to perform the ray interpolation. Furthermore, the data in the light-ray data, which is closest to the ray to be acquired, may be used to perform the ray interpolation.

When the ray from the virtual image pickup position is not caught by the image pickup device, the intersection of the ray and a camera plane arbitrarily defined in a three-dimensional space may be calculated and the group of rays caught at image pickup positions near the intersection may be used to perform the ray interpolation. The rays used in the ray interpolation are preferably emitted from the same spatial point as the ray to be acquired.

However, the depth of the spatial point is ordinarily unknown. Accordingly, a reference depth plane is generally provided at a predicted position of the object (for example, the center of gravity of the object), and it is presumed that all the spatial points are on the reference depth plane and that all the rays are emitted from the reference depth plane. The ray emitted from the intersection of the ray to be acquired and the reference depth plane is selected from among the group of the rays caught at image pickup positions near the virtual image pickup position, and the selected ray is used in the ray interpolation. The arbitrary viewpoint image is generated by such ray interpolation.

Referring back to FIG. 8A, in Step S803, the CPU 2021 determines the movement range of the radiation source and the interval between the positions of the radiation source. Specifically, the CPU 2021 calculates and determines the movement range of the radiation source based on information including the allowable movement range of the viewpoint determined in Step S801, the three-dimensional display parameters, and the focal length (the angle of view) of the arbitrary viewpoint image. The CPU 2021 also calculates and determines an interval between the positions of the radiation source based on the information concerning the quality level of the arbitrary viewpoint image to be generated, determined in Step S802.

As the movement range of the radiation source, the CPU 2021 calculates a range required to cover the group of the rays used for forming the arbitrary viewpoint images corresponding to all the viewpoints capable of being selected within the allowable movement range of the viewpoint.

FIGS. 10A and 10B illustrates the relationship between the allowable movement range of the viewpoint and the movement range of the radiation source. Referring to FIGS. 10A and 10B, the movement range of the radiation source is defined on a plane (radiation source plane) 1001 where the radiation source moves. Reference numeral 301 denotes an image pickup device (radiation receiving surface) and reference numeral 302 denotes an object. A rectangular allowable movement range 1002 of the viewpoint is shown by a broken line. The allowable movement range 1002 of the viewpoint has representative points (four corners) 1003. Reference numeral 1004 denotes a virtual image plane when the representative points 1003 in the allowable movement range 1002 of the viewpoint are set as the virtual radiation source positions. In order to generate from the light-ray data the rear-projected image to be formed on the virtual image plane 1004 by irradiation with a light ray (although the light ray is a radiation ray according to the second embodiment, the radiation ray is referred to as the light ray for convenience) from the virtual radiation source position (the representative points 1003), it is necessary to define the movement range of the radiation source so as to cover all the rays forming the rear-projected image. Specifically, positions where light rays 1005 intersect with the radiation source plane 1001 and which are shifted from the center of the radiation source plane 1001 are set as outer ends of the movement range of the radiation source. A movement range 1006 of the radiation source is determined in the above manner.

The interval between the positions of the radiation source is determined in accordance with the quality level of the arbitrary viewpoint image to be generated, in the ray interpolation performed for the generation of the arbitrary viewpoint image, such that there is a considerably minor error of an interpolation light ray (a light ray used in the interpolation) with respect to the light ray to be acquired. The density of the ray space data given by the pickup and storage of the parallax images is adjusted based on the quality level of the arbitrary viewpoint image to be generated.

Increasing the density of the ray space data and shortening the interpolation interval can generate the arbitrary viewpoint image forming a superior stereoscopic image. In contrast, decreasing the density of the ray space data and lengthening the interpolation interval reduces the quality level of the stereoscopic image.

Figure 9:
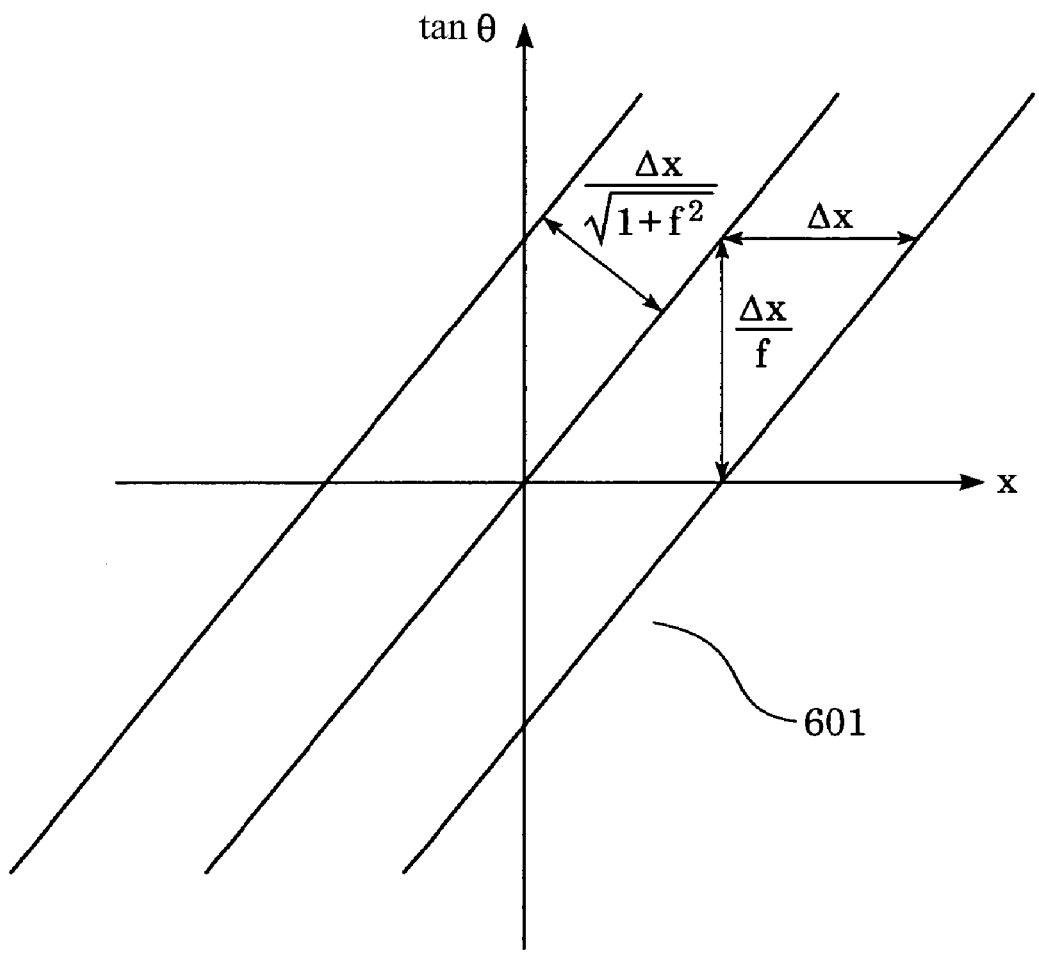
FIG. 9 illustrates light-ray data.

Although only horizontal variation of the light rays is considered for simplicity, the following description is applicable to a case in which vertical variation of the light rays is also considered. The stored light-ray data has relationship shown in FIG. 9. When the radiation source is moved in the radiation source plane parallel to the reference depth plane to pick up images and the light-ray data is stored, the light-ray data corresponding to the positions of the radiation source and the radiation receiving surface is mapped on a straight line having a gradient of 1/f in an x, tan θ space 601, which is the light-ray data space, where f denotes the distance between the radiation source and the radiation receiving surface. Accordingly, straight lines on which the data on the light rays emitted from the radiation sources arranged at positions having the same distance to the radiation receiving surface is mapped are parallel to each other in the x, tan θ space, and the intervals between the straight lines corresponds to the interval Δx between the positions of the radiation source. Adjusting the interval Δx between the straight lines can control the relationship between the quality level of the arbitrary viewpoint image to be generated and the interval between the positions of the radiation source.

In other words, the interval between the positions of the radiation source is set such that the distance between the interpolation light ray and an interpolated light ray that is generated by the interpolation in a parameter space (a light ray space) is always set to a value not longer than a predetermined threshold. An image quality coefficient a is used for adjusting the quality level of an image, corresponding to the quality level of the arbitrary viewpoint image to be generated. For example, the image quality coefficient a is set to a smaller value in order to increase the quality level of the arbitrary viewpoint image to be generated whereas the image quality coefficient is set to a larger value in order to decrease the quality level of the arbitrary viewpoint image to be generated. By experiment, setting the image quality coefficient a to a value of the order of one to three pixels can suppress reduction in the quality level of the arbitrary viewpoint image to be generated.

The ray interpolation by using the pixels corresponding to the horizontally adjoining viewpoints, the ray interpolation by using the pixels corresponding to the vertically adjoining viewpoints, the ray interpolation by using the closest pixel, and the ray interpolation by using an arbitrary reference depth plane have been exemplified as the ray interpolation methods. The relationship between the information concerning the density of the light-ray data and the interval between the positions of the radiation source in the above ray interpolation methods is described next.

The interval between the straight lines in an x direction is equal to $\Delta x$ and the interval therebetween in a tan θ direction is equal to $\Delta x/f$. A maximum interval between the straight lines is equal to $\Delta x \cdot (1+f^2)^{-1/2}$. When these intervals are interpolated by the above ray interpolation methods, restricting the interval $\Delta x$ between the positions of the radiation source within an interval a corresponding to the image quality coefficient maintains the deterioration of the generated image due to the interpolation below a predetermined level.

The minimum interval between the positions of the radiation source in the acquisition of the light-ray data is set so as to satisfy Formula 7 in the ray interpolation by using the pixels corresponding to the horizontally adjoining viewpoints.

$$dx = \Delta x < a \qquad \text{[Formula 7]}$$

The minimum interval between the positions of the radiation source in the acquisition of the light-ray data is set so as to satisfy Formula 8 in the ray interpolation by using the pixels corresponding to the vertically adjoining viewpoints.

$$dy = \Delta x/f < a \qquad \text{[Formula 8]}$$

$$\Delta x < f a$$

The minimum interval between the positions of the radiation source in the acquisition of the light-ray data is set so as to satisfy Formula 9 in the ray interpolation by the closest pixel.

$$d_{minDistance} = \Delta x \cdot (1+f^2)^{-1/2} < a$$

$$\Delta x < (1+f^2)^{1/2} \cdot a \qquad \text{[Formula 9]}$$

In the interpolation with two light rays by the ray interpolation using an arbitrary reference depth plane, which ray interpolation produces a superior result, it is possible to control the relationship between the quality of the mage to be rendered and the interval between the positions of the radiation source based on Formula 10.

[Formula 10]

$$\Delta x \leq \frac{z_0}{|Z - z_0|} \Delta \varepsilon$$

Figure 11:
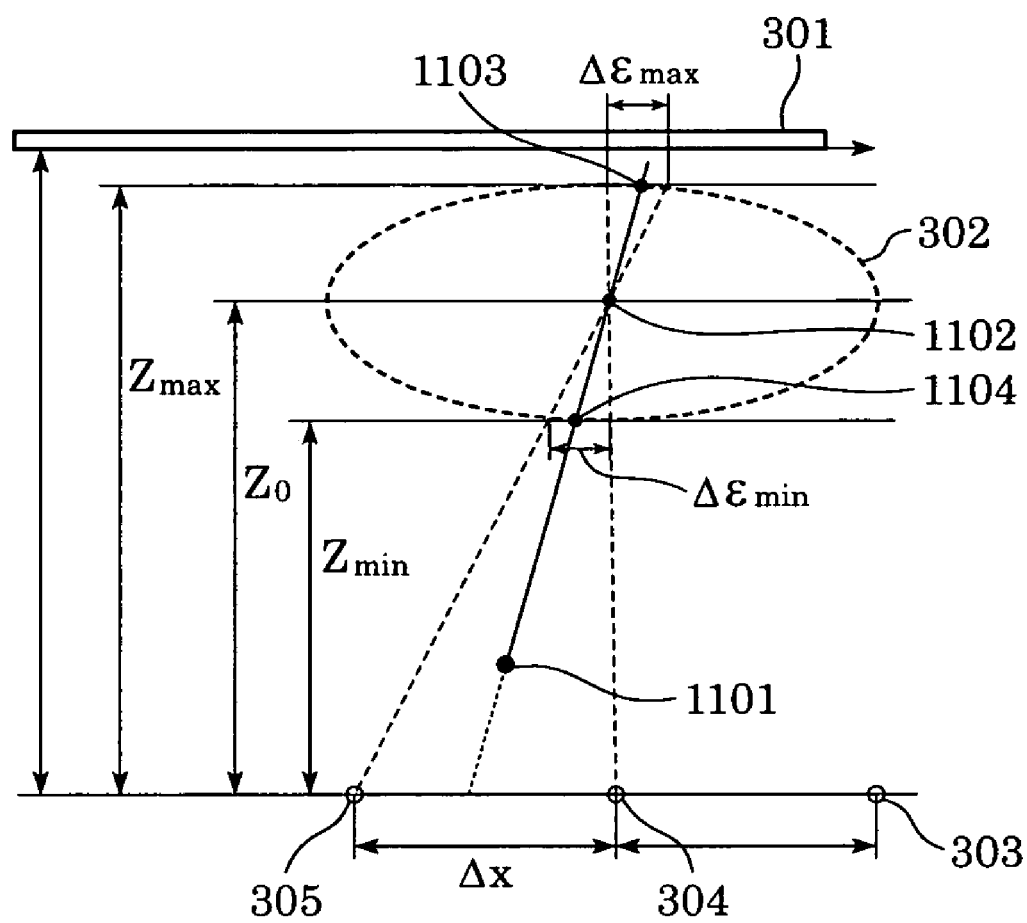
FIG. 11 is a schematic diagram illustrating ray interpolation for forming an image at a virtual radiation source position in the generation of the arbitrary viewpoint image, according to the second embodiment of the present invention.

Formula 10 indicates the relationship between an allowable interval $\Delta \epsilon$ of the radiation rays and the interval $\Delta x$ between the positions of the radiation source on the true object surface in the interpolation with respect to the reference depth plane. The relationship is described next with reference to FIG. 11. FIG. 11 is a schematic diagram illustrating the interpolation with two light rays by the ray interpolation using an arbitrary reference depth plane.

Referring to FIG. 11, reference numeral 301 denotes an image pickup device (radiation receiving surface) and reference numeral 302 denotes an object. Reference numerals 303, 304, and 305 denote the positions of the radiation source, spaced $\Delta x$ apart. The scope of the object 302 is an area between a distance $Z_{max}$ from a plane (radiation source plane) on which the radiation source is provided and a distance $Z_{min}$ therefrom. The reference depth plane is apart from the radiation source plane by a distance z0.

Reference numeral 1101 denotes a virtual radiation source position where the parallax image corresponding to a virtual viewpoint is formed. When a solid line extending from the virtual radiation source position 1101 shows a light ray to be interpolated (the interpolated light ray), the interpolation light rays used for the interpolation of the interpolated light ray are two light rays that are emitted from the two positions of the radiation source, closest to the position on the radiation source plane, to which position the interpolated light ray extends, and that intersect with the interpolation light ray at the same coordinate on the reference depth plane. Referring to FIG. 11, two broken lines extending from the positions 304 and 305 of the radiation source corresponds to the interpolation light rays.

When one spatial point representing the object 302 is a spatial point 1102 on the reference depth plane, the data concerning the interpolated light ray is acquired as the data concerning the light ray passing through the spatial point 1102 based on the geometrical relationship with the two interpolation light ray.

However, when a spatial point 1103 at a maximum depth $Z_{max}$ in the scope of the object and a spatial point 1104 at a minimum depth $Z_{min}$ therein are to be calculated by the ray interpolation, the interval between the two interpolation light rays sandwiching the interpolated points (1103 and 1104) is often maximized in the scope of the object. The maximum interval between the interpolation light rays (image pickup light rays) is expressed by $\Delta \epsilon$ ($\Delta \epsilon_{max}$, $\Delta \epsilon_{min}$).

In such a case, assigning a depth Z having a larger absolute value of the difference from z0, among the minimum depth $Z_{min}$ and the maximum depth $Z_{max}$ in the scope of the object, and a maximum allowable interval $\Delta \epsilon$ between the image pickup light rays in Formula 10 gives a minimum interval $\Delta x$ between the positions of the radiation source.

An interval $\Delta x'$ between the positions of the radiation source with respect to a light ray that is emitted from the virtual radiation source position and is projected on the radiation receiving surface through the object 302 is expressed by Formula 11 using the image quality coefficient a.

$$\Delta x' \leq \Delta x \cdot a \qquad \text{[Formula 11]}$$

Hence, adjusting the image quality coefficient a can adjust the balance between the image pickup efficiency and the image quality level.

When $\Delta \epsilon$ denotes a size that does not cause aliasing on a rendering surface, Formula 12 is satisfied.

[Formula 12]

$$\Delta \varepsilon \leq \frac{|Z - Z_{obs}|}{2L} \Delta u_{obs}$$

In Formula 12, $Z_{obs}$ denotes the interval between the positions of the radiation source, where the arbitrary viewpoint image is generated, and the camera plane, and $\Delta u_{obs}$ denotes the interval between the pixels on the rendering surface.

As described above, the interval between the positions of the radiation source can be controlled by assuming an expression that associates the data interval of the light-ray data with the quality of the arbitrary viewpoint image to be rendered, depending on the interpolation method of the ray space data, and by varying the image quality coefficient a used for adjusting the data interval of the ray space data by using the presumed expression. Increasing the image quality coefficient a increases the interval between the positions of the radiation source but reduces the quality of the generated image. In contrast, decreasing the image quality coefficient a improves the quality of the generated image. However, in the latter case, it is necessary to pick up more input images because the interval between the positions of the radiation source is short.

The expression that associates the data interval of the light-ray data, that is, the interval between the positions of the radiation source, with the quality of the arbitrary viewpoint image may be any expression as long as it can correctly associates the interval between the positions of the radiation source with the quality of the arbitrary viewpoint image.

Referring back to FIG. 8, in Step S804, the CPU 2021 causes the radiation source to emit the radiation ray while causing the radiation source to sequentially move in the movement range of the radiation source and at the interval between the positions of the radiation source, determined in Step S803, and sequentially picks up the parallax images, which are the rear-projected images of the object 302, with the image pickup device 301.

In Step S805, the CPU 2021 stores the data concerning the group of parallax images picked up in Step S804 in the mass storage device 2022 or the database 208 on the network or stores the data in an external storage device through the input-output device 203. After storing the data, the image-pickup and storage process is completed.

FIG. 8B is a flowchart showing the operation in the stereoscopic-image generation and display process. The following processing is performed when the arbitrary viewpoint images are to be displayed in the three-dimensional display 206 and when the viewpoint and/or the zoom ratio are varied after the arbitrary viewpoint images are displayed.

In Step S806, the CPU 2021 acquires the three-dimensional display parameters. Specifically, the CPU 2021 acquires varied parameters, among the three-dimensional display parameters including the number of viewpoint of the three-dimensional display 206, the estimated observation distance, the angle of view, the interval between binocular viewpoints, the three-dimensional effect, the observation viewpoint position (the coordinate of the observer's eye), the zoom ratio, and the critical range of the three-dimensional effect. However, when no three-dimensional display parameter is acquired (the first routine immediately after the startup), all the three-dimensional display parameters are acquired.

The CPU 2021 acquires these three-dimensional display parameters by reading the values input by the observer with the input device 205 or by reading a file including the three-dimensional display parameters through the input-output device 203. The observer inputs the values while referring to the values displayed on the console of the operation display 204 or while observing the stereoscopic image displayed in the three-dimensional display 206. The observation viewpoint position may be set to an estimated typical value or may be updated when, for example, the vision sensor detects any variation in the position where the observer is located.

In Step S807, the CPU 2021 determines the virtual radiation source position. Specifically, the CPU 2021 determines virtual viewpoint positions used for forming the stereoscopic image and determines a plurality of virtual radiation source positions appropriate for the three-dimensional display parameters corresponding to the virtual viewpoint positions.

In Step S808, the CPU 2021 generates the arbitrary viewpoint image. Specifically, the CPU 2021 selects a parallax image (arbitrary viewpoint image) corresponding to the virtual radiation source positions determined in Step S807 from among the data concerning the group of parallax images stored in Step S805.

When the parallax image corresponding to the virtual radiation source positions does not exist in the stored group of parallax images, the stored parallax images are used to perform the ray interpolation described above in order to generate (render) a new arbitrary viewpoint image corresponding to the virtual radiation source positions. For example, the CPU 2021 extracts the light rays corresponding to the virtual radiation source positions from the light-ray data stored in the mass storage device 2022 and generates a new arbitrary viewpoint image in the main memory device 2023 or the mass storage device 2022.

In Step S809, the CPU 2021 performs conversion to stereoscopic image data. The CPU 2021 synthesizes the group of parallax images in accordance with the pixel array in the three-dimensional display 206 by using the arbitrary viewpoint images selected or generated in Step S808 to generate the stereoscopic image data. Specifically, the CPU 2021 generates the stereoscopic image data by the multiplexing in which pixel information is sampled from each parallax image and the sampled pixel information is synthesized.

In Step S810, the CPU 2021 confirms whether the stereoscopic image data generated in Step S809 is to be stored in the mass storage device 2022. If the stereoscopic image data is to be stored, in Step S811, the CPU 2021 stores the stereoscopic image data in the mass storage device 2022 or in the database 208 on the network.

Since the generation of a superior arbitrary viewpoint image imposes a heavy processing load on the CPU 2021, it is difficult to rapidly display such a superior image without high-performance (and, generally, expensive) hardware. To address this problem, creating a stream for moving an arbitrary viewpoint in advance is useful for the observer who wants to smoothly observe the stereoscopic image.

In Step S812, the CPU 2021 displays the stereoscopic image data generated in Step S809 in the three-dimensional display 206. In the display in Step S812, the stereoscopic image data may be output as print data to the printer 207, instead of displaying the stereoscopic image in the three-dimensional display 206. When the stereoscopic image data is output as print data, both in the case of directly printing the stereoscopic image data on an optical material, such as a lenticular sheet or an integral sheet, and in the case of printing the stereoscopic image data on a recording medium having such optical materials combined therein, it is preferable to perform the processing in Step S806 and subsequent steps again in order to generate stereoscopic image data appropriate for the print parameters of the optical material. Performing the processing from the beginning provides a superior stereoscopic image, compared with a case in which the stereoscopic image data generated in accordance with the three-dimensional display parameters of the three-dimensional display is printed.

In Step S813, the CPU 2021 determines whether the processing is completed. After the stereoscopic image is displayed, the processing is completed. If the three-dimensional display parameters are changed due to the movement of the virtual radiation source positions or an operation of the observer, the CPU 2021 returns to Step S806 to repeat the stereoscopic-image generation and display process for selecting or generating an arbitrary viewpoint image again to display the stereoscopic image.

Although a case in which the image pickup device 301 is fixed and the radiation source is moved is described in the second embodiment, switching between multiple radiation sources may change the radiation source that emits the radiation rays. The position of the radiation source may be fixed and the image pickup device may be moved, or switching between multiple image pickup devices may change the image pickup device that picks up images. Alternatively, both the radiation source and the image pickup device may be moved.

According to the stereoscopic-image generating system and the control method thereof according to the above embodiments, the radiation source moves with respect to the image pickup device in accordance with the presentation parameters indicating, for example, the performance of the presentation device and the presentation request of the observer when rear-projected images are picked up. Accordingly, it is possible to easily present stereoscopic images having natural stereoscopic view with various presentation devices.

According to the stereoscopic-image generating system and the control method thereof according to the above embodiments, an image in accordance with the presentation parameter indicating, for example, the performance of the presentation device and the presentation request of the observer is selected from among multiple rear-projected images that has been picked up and stored to present a stereoscopic image based on the selected image, so that it is possible to easily generate arbitrary viewpoint images having natural stereoscopic view with various presentation devices.

Furthermore, determining a relative movement range of the radiation source and the image pickup device based on the allowable movement range of the viewpoint from which the stereoscopic image is observed, when rear-projected images are picked up, and/or determining a relative position of the radiation source with respect to the image pickup device in accordance with the image quality required for the stereoscopic image, when rear-projected images are picked up, achieve efficient image pickup and presentation of the stereoscopic image having a quality level higher than a predetermined level.

While the present invention has been described with reference to exemplary embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

This application claims priority from Japanese Patent Application No. 2004-176153 filed Jun. 14, 2004, which is hereby incorporated by reference herein.

What is claimed is:

1. A stereoscopic-image generating system comprising:
    an X-ray radiation source;
    an image pickup device adapted to acquire information on a transmissive X-ray transmitted through an object, the transmissive X-ray being emitted from the X-ray radiation source; and
    a control device adapted to acquire presentation parameters of a presentation device which present a stereoscopic image based on the information on the transmissive X-ray and to control a relative position of the X-ray radiation source with respect to the image pickup device in the acquisition of the information on the transmissive X-ray based on the presentation parameters, wherein the presentation parameters are specific to the presentation device.

2. A stereoscopic-image generating system according to claim 1,
    wherein the parameters specific to the presentation device includes the value relating to at least one of a number of observation viewpoints, an observation distance, an interval between binocular viewpoints, an angle of view, a three-dimensional effect, and a zoom ratio in the presentation device.

3. The stereoscopic-image generating system according to claim 1, wherein the presentation parameters are in the group consisting of a number of observation viewpoints, an observation distance, an interval between binocular viewpoints, a three-dimensional effect, and a zoom ratio in the presentation device.

4. A control method of a stereoscopic-image generating system including an image pickup device that acquires information on a transmissive X-ray transmitted through an object, the transmissive X-ray being emitted from an X-ray radiation source, the control method comprising:
    acquiring presentation parameters of a presentation device that presents a stereoscopic image based on the information on the transmissive X-ray; and
    controlling a relative position of the X-ray radiation source with respect to the image pickup device in the acquisition of the information on the transmissive X-ray based on the presentation parameters, wherein the presentation parameters are specific to the presentation device.

5. A control method according to claim 4,
    wherein the parameters specific to the presentation device includes the value relating to at least one of a number of observation viewpoints, an observation distance, an interval between binocular viewpoints, an angle of view, a three-dimensional effect, and a zoom ratio in the presentation device.

6. Computer-executable process steps for causing a computer to execute the control method according to claim 4.

7. The control method according to claim 4, wherein the presentation parameters are in the group consisting of a number of observation viewpoints, an observation distance, an interval between binocular viewpoints, a three-dimensional effect, and a zoom ratio in the presentation device.

* * * * *